United States Patent
Dharmatilleke et al.

(10) Patent No.: US 12,238,267 B2
(45) Date of Patent: Feb. 25, 2025

(54) DEVICE TO CREATE AND DISPLAY FREE SPACE HOLOGRAM

(71) Applicants: Medha Dharmatilleke, Singapore (SG); Nanayakkara Dharmatilleke, Singapore (SG)

(72) Inventors: Medha Dharmatilleke, Singapore (SG); Nanayakkara Dharmatilleke, Singapore (SG)

(73) Assignee: Medha Dharmatilleke, Singapore (SG)

( * ) Notice: Subject to any disclaimer, the term of this patent is extended or adjusted under 35 U.S.C. 154(b) by 380 days.

(21) Appl. No.: 17/790,756

(22) PCT Filed: Jul. 12, 2020

(86) PCT No.: PCT/SG2020/050398
§ 371 (c)(1),
(2) Date: Jul. 4, 2022

(87) PCT Pub. No.: WO2021/137752
PCT Pub. Date: Jul. 8, 2021

(65) Prior Publication Data
US 2023/0035915 A1    Feb. 2, 2023

(30) Foreign Application Priority Data
Jan. 5, 2020   (SG) .......................... 10202000067Y

(51) Int. Cl.
*H04N 13/302* (2018.01)
*A61B 90/00* (2016.01)
(Continued)

(52) U.S. Cl.
CPC ........... *H04N 13/302* (2018.05); *A61B 90/37* (2016.02); *G02B 26/0875* (2013.01);
(Continued)

(58) Field of Classification Search
CPC ..... G06T 11/60; G06T 15/005; G06T 19/006; G06T 2200/04; G06T 2200/24;
(Continued)

(56) References Cited

U.S. PATENT DOCUMENTS 6,166,834 A    12/2000  Taketomi et al.
10,073,268 B2 * 9/2018  Alexander ........... H04N 9/3129
(Continued)

FOREIGN PATENT DOCUMENTS

WO    2015-192117 A1    12/2015
WO    2017-196399 A1    11/2017

OTHER PUBLICATIONS

Yue Zengji, et al.: "Nanometric Holograms Based on a Topological Insulator Material", Nature Communications, vol. 8, No. 1, Aug. 1, 2017 (Aug. 1, 2017), XP055825049, Doi: 10.1038/ncomms15354.

*Primary Examiner* — Ming Wu
(74) *Attorney, Agent, or Firm* — Andrew A Paul

(57) ABSTRACT

A unique method and a device to generate free space "pop-out" & "sink-in" holograms is disclosed herein. The hologram disclosed herein does not use any special medium, mirrors, reflective screens or wearables such as headgear & special glasses. The hologram disclosed herein can be created in free space, outer space or in air, without any other optical components except for the special display screen of the hologram device. This device demonstrates a free space hologram and the hologram Augmented Reality & hologram Virtual Reality. A camera capable of hologram quality images equipped with a smart lens which mimics the human eye by changing it's lens aperture according to the light intensity as the pupil of the human eye and focus & capture "pop-out" & "sink-in" hologram images is disclosed herein. The audio which is incorporated with the device provide multi dimensional multi directional audio effects.

20 Claims, 20 Drawing Sheets

(51) Int. Cl.
    *G02B 26/08*     (2006.01)
    *G02B 30/56*     (2020.01)
    *G03H 1/00*     (2006.01)
    *G03H 1/22*     (2006.01)
    *G04G 9/00*     (2006.01)
    *G06F 3/01*     (2006.01)
    *G06T 19/00*     (2011.01)
    *G09B 5/02*     (2006.01)
    *G09B 9/08*     (2006.01)
    *G09B 23/30*     (2006.01)
    *H04M 1/02*     (2006.01)
    *H04M 1/72448*     (2021.01)
    *H04N 13/218*     (2018.01)
    *H04N 13/236*     (2018.01)
    *H04N 13/243*     (2018.01)
    *H04N 13/293*     (2018.01)
    *H04N 13/359*     (2018.01)
    *H04S 1/00*     (2006.01)

(52) U.S. Cl.
    CPC ........... *G02B 30/56* (2020.01); *G03H 1/0005* (2013.01); *G03H 1/2205* (2013.01); *G04G 9/007* (2013.01); *G06T 19/006* (2013.01); *H04N 13/218* (2018.05); *H04N 13/236* (2018.05); *H04N 13/243* (2018.05); *H04N 13/293* (2018.05); *H04N 13/359* (2018.05); *H04S 1/00* (2013.01); *G03H 2001/0088* (2013.01); *G06F 3/015* (2013.01); *G06F 3/017* (2013.01); *G09B 5/02* (2013.01); *G09B 9/08* (2013.01); *G09B 23/30* (2013.01); *H04M 1/026* (2013.01); *H04M 1/72448* (2021.01); *H04N 2213/001* (2013.01)

(58) Field of Classification Search
    CPC . G06T 3/20; G06K 19/16; G06K 7/10; G06K 7/10732; G06K 7/1404
    See application file for complete search history.

(56) References Cited

U.S. PATENT DOCUMENTS

| | | | |
|---|---|---|---|
| 2007/0035829 A1* | 2/2007 | Woodgate | G02B 30/27 348/E13.044 |
| 2014/0226900 A1 | 8/2014 | Saban et al. | |
| 2016/0033771 A1* | 2/2016 | Tremblay | G02B 26/10 359/851 |
| 2016/0103321 A1* | 4/2016 | An | H04N 13/398 348/40 |
| 2016/0109851 A1 | 4/2016 | Tsang | |
| 2017/0090420 A1* | 3/2017 | Rotschild | G02B 30/56 |
| 2017/0244890 A1* | 8/2017 | Lee | H04N 23/667 |
| 2018/0088346 A1* | 3/2018 | Willden | H04N 13/111 |
| 2019/0155033 A1* | 5/2019 | Gelman | G02B 27/0093 |
| 2019/0258061 A1 | 8/2019 | Solomon | |

* cited by examiner

Top view of Fig.28

DEVICE TO CREATE AND DISPLAY FREE SPACE HOLOGRAM

CROSS REFERENCE TO RELATED APPLICATION

This application is a national stage application under 35 USC § 371 of PCT/SG2020/050398, filed 12 Jul. 2020, the disclosure of which is hereby incorporated by reference in its entirety.

BACKGROUND

Technical Field

Embodiments of the invention relate to free space holograms with no headgear or wearables and hologram camera lenses.

Description of Related Art

Up to now, all the so called available holograms have to be viewed from a very limited certain position or with the aid of some reflective medium or mirrors (0102) in order to project a light beam and get it's reflection or to get the reflection of the image displayed in a display panel (0101) or in other words to get the reflected light rays back to the observer's eyes. The presently available so called holograms (0103) are created within the reflective medium or the hologram is seen as if it is behind the surface of the mirror as in FIG. 1 and FIG. 2.

There is no prior art related to any device which truly generate free space holograms, except in science fiction stories and movies. The holograms which are prior art use mirrors or some kind of reflective medium to form a reflection of a picture which is displayed in a 2 dimensional display screen or the reflection of an image projected onto some medium which has reflective or refractive optical properties and therefore, these are not true free space holograms. Further, Augmented Reality (AR) and Virtual Reality (VR) devices using headgear and eye glasses available at present, provide isometric images or 2-Dimensional X, Y perspective images on top of a two-Dimensional live image captured by the camera, which is still a flat 2D image, although they are marketed as 3D. There is no related art on the optical unit disclosed herein.

SUMMARY OF EMBODIMENTS OF THE INVENTION

The invention disclosed herein discloses a method and a device which produce a ground-breaking 3-Dimensional high definition free space hologram where the free space "pop-out" & "sink-in" hologram can be viewed from all directions and can do a walkthrough, or put the hand through the free space "pop-out" & "sink-in" hologram. Further, the free space "pop-out" & "sink-in" hologram disclosed herein does not use any special medium such as smoke, mirrors, reflective screens or wearables such as headgear & special glasses. The camera which this device may use to capture free space "pop-out" & "sink-in" hologram quality images and videos may use lenses which has a combination of rings of photochromic or thermochromic or magnetochromic or electrochromic material. Further, the invention discloses herein the "free space hologram Augmented reality (AR)" and "Free space hologram Virtual reality (VR)" and "Free space hologram Mixed Reality (MR)" experience. The free space Augmented reality experience is such that this method and device provide an experience such as the "Hollow deck" in the science fiction movie "star Trek", on a mobile device/Television screen or on a specially designed wall, floor or roof. The device can be used for simultaneous viewing of "pop out" or "sink in" hologram "pop-out" & "sink-in" Augmented reality (AR), Virtual reality (VR) and Mixed reality (MR) by multiple people, with a single device.

When the hologram device disclosed herein is operated in free space "pop-out" & "sink-in" hologram augmented reality mode, the objects, persons or anything that is inserted into the image captured live by the camera, will have the perception of three dimensions mainly X, Y and Z, where Z coordinate will determine the "pop out" or "sink in" aspect of the real augmented reality experience. The "pop out" being referred to as being able to observe the artificially introduced objects or persons, as if they are located outside the surface of the AR device's screen. Similarly, "sink in" being referred to as being able to observe the artificially introduced objects or persons, as if they are located below the surface of the AR device's screen or inside the AR device's screen.

The audio which is incorporated with the device provide multi dimensional multi directional audio effects which gives a natural feel to the free space "pop-out" & "sink-in" hologram device.

The invention presented here details a method and a device where the hologram can be viewed from any direction, without any reflective mirrors, reflective mediums, reflective screens or wearable glasses or headgear. The hologram disclosed herein is created in free space or in other words, in air, without any other optical components except for the special display screen of the mobile device or the television or the computer monitor or smart watch or illuminated photo or illuminated picture disclosed herein.

This is the first ever invention which has practically shown a free space hologram created in space as shown in FIG. 3.

The free space "pop-out" & "sink-in" hologram display disclosed herein can be either an active "pop-out" & "sink-in" display, where electric power is used, or a passive "pop-out" & "sink-in" display, where electric power is not used.

DETAILED DESCRIPTION OF ILLUSTRATIVE EMBODIMENTS

Figure 1:
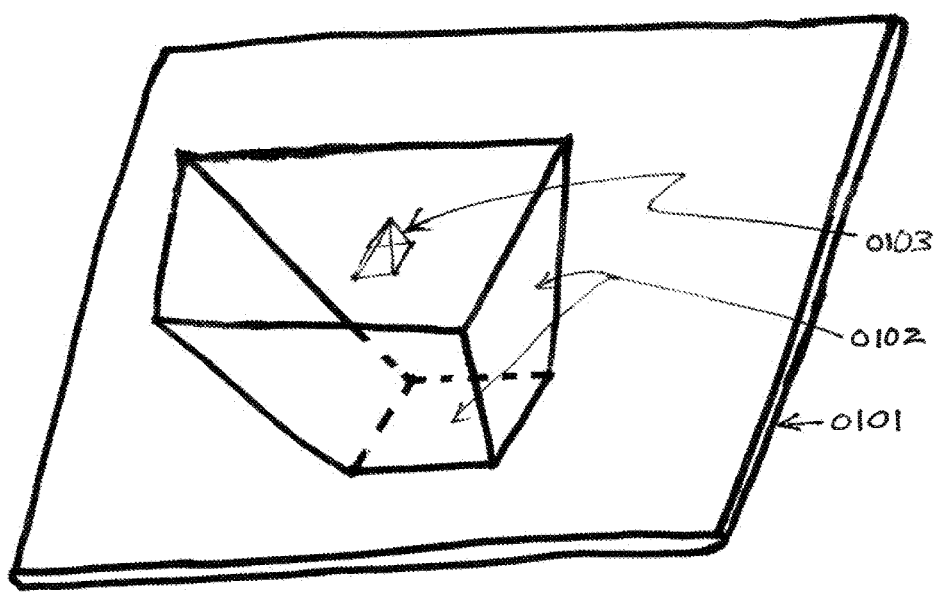
FIG. 1 illustrates a mirror attached on top of the image display screen.
Figure 2:
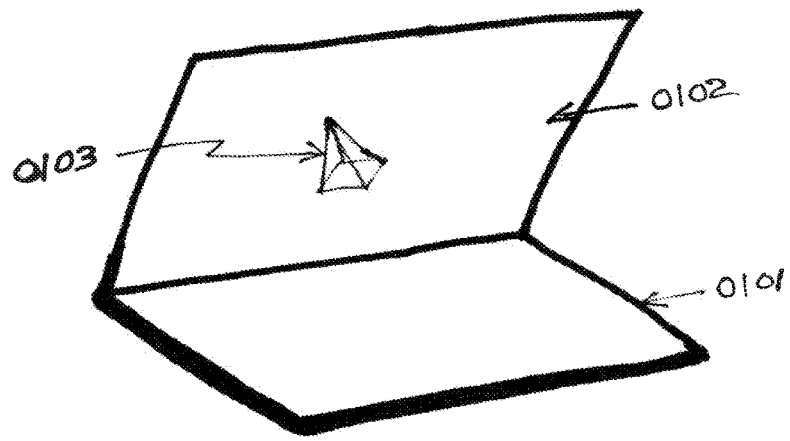
FIG. 2 illustrates a mirror attached on top of the image display screen.
Figure 3:
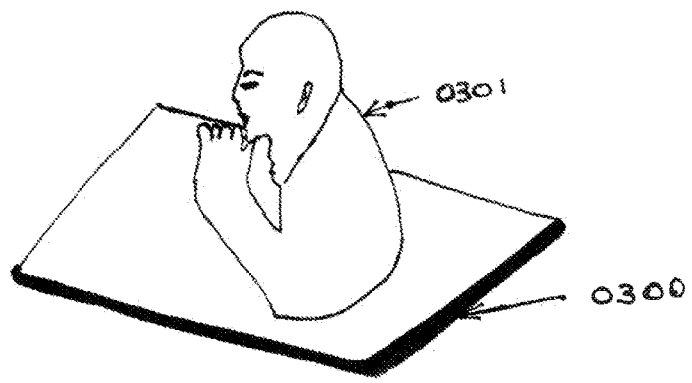
FIG. 3 illustrates the free space "pop-out" & "sink-in" hologram on the free space "pop-out" & "sink-in" display device or screen.
Figure 4:
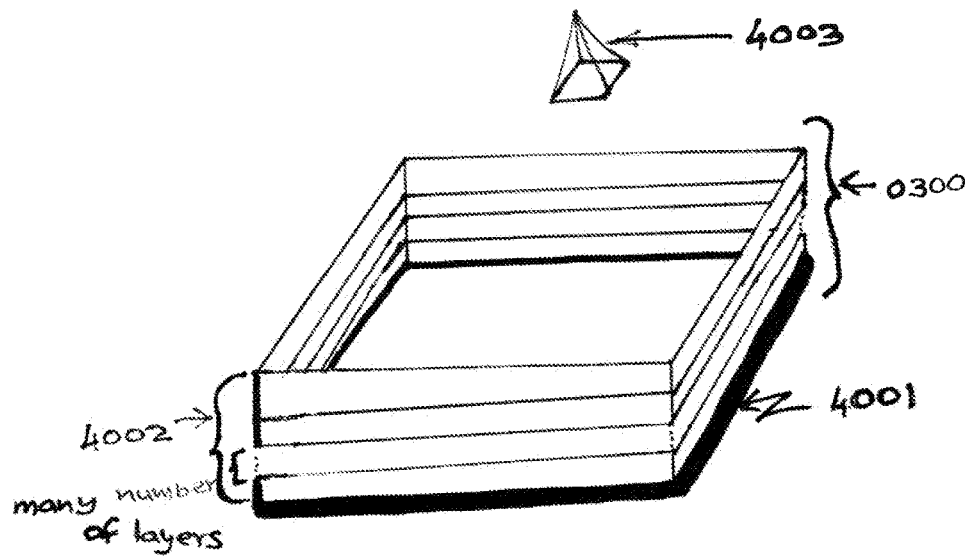
FIG. 4 illustrates the important components of the structure of the free space "pop-out" & "sink-in" hologram screen.
Figure 4A:
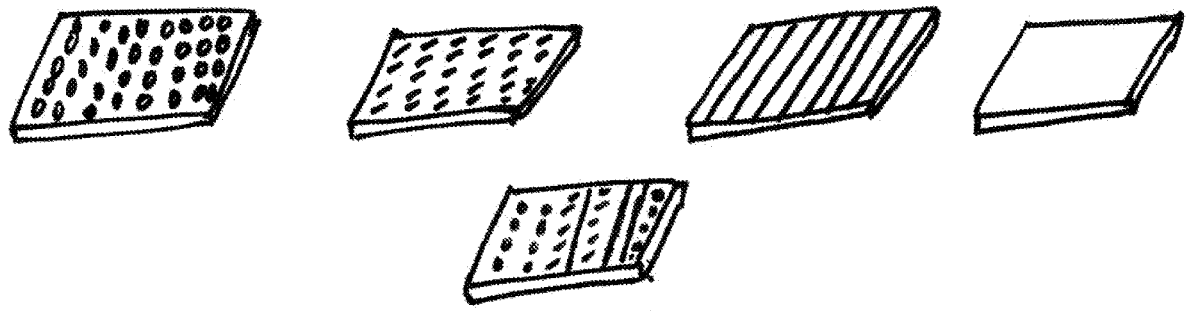
FIG. 4a illustrates possible compositions of the layers (4002) of FIG. 4, but not limited to these.
Figure 5:
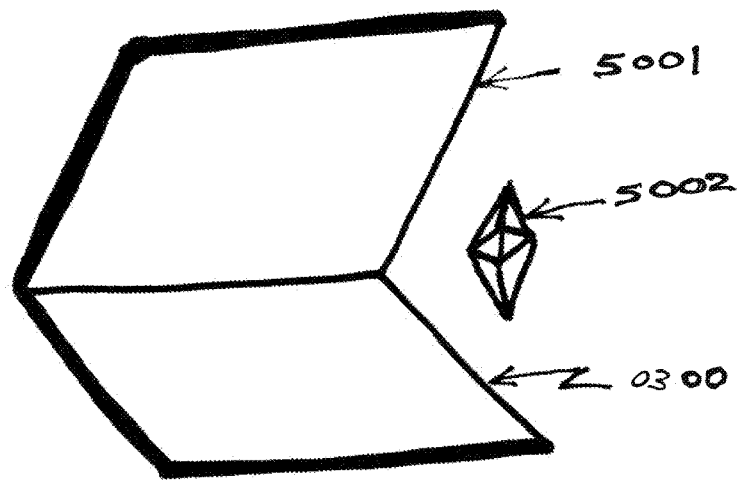
FIG. 5 illustrates the free space "pop-out" & "sink-in" hologram display being used with single or multiple mirrors to give special effects to the free space "pop-out" & "sink-in" hologram.
Figure 6:
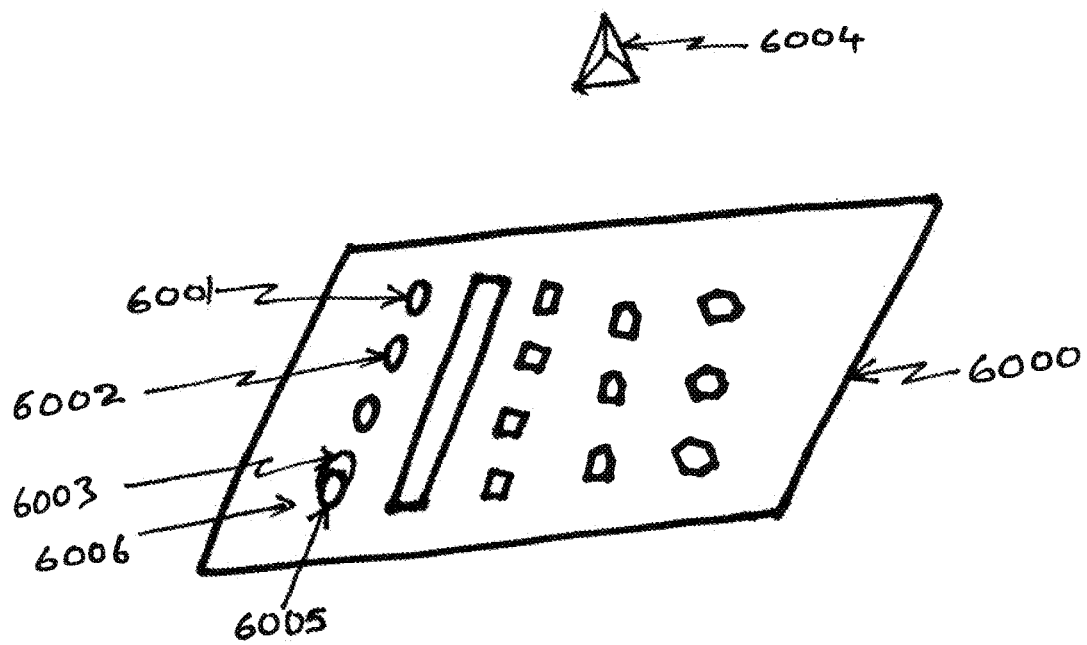
FIG. 6 illustrates liquid lenses or lens arrays are formed on the surface of the display screen in order to create the free space "pop-out" & "sink-in" hologram.
Figure 7:
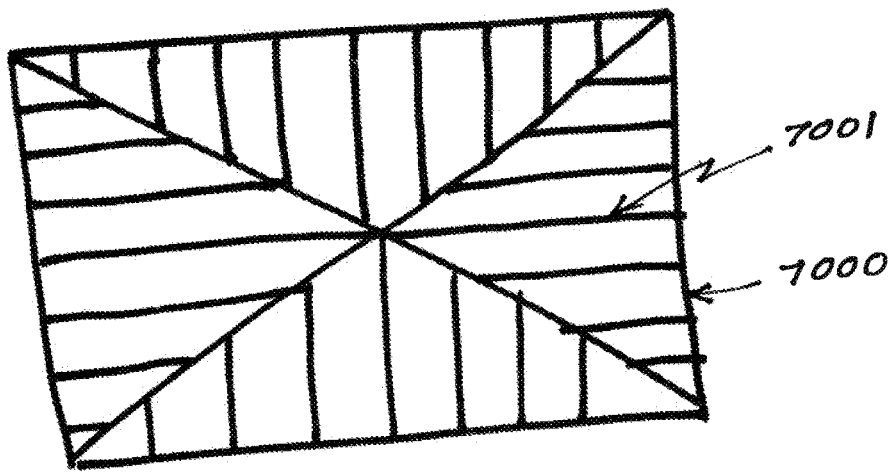
FIG. 7 illustrates the optical patterns or array of optical lenses or material or structures made on top of the display screen in multiple directional patterns in order to make full round free space "pop-out" & "sink-in" hologram where the observer can view the front, back, two sides' views by walking around the free space hologram
Figure 8:
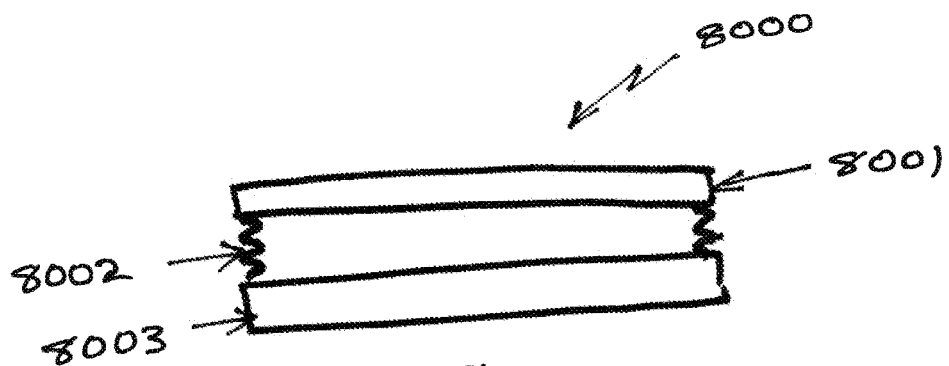
FIG. 8 illustrates the array of structures or array of lenses or array of actuators or optical & electromagnetic/electrostatic components which may be moved with respect to the display screen by means of an electrostatic actuator or electromagnetic actuator.
Figure 9A:
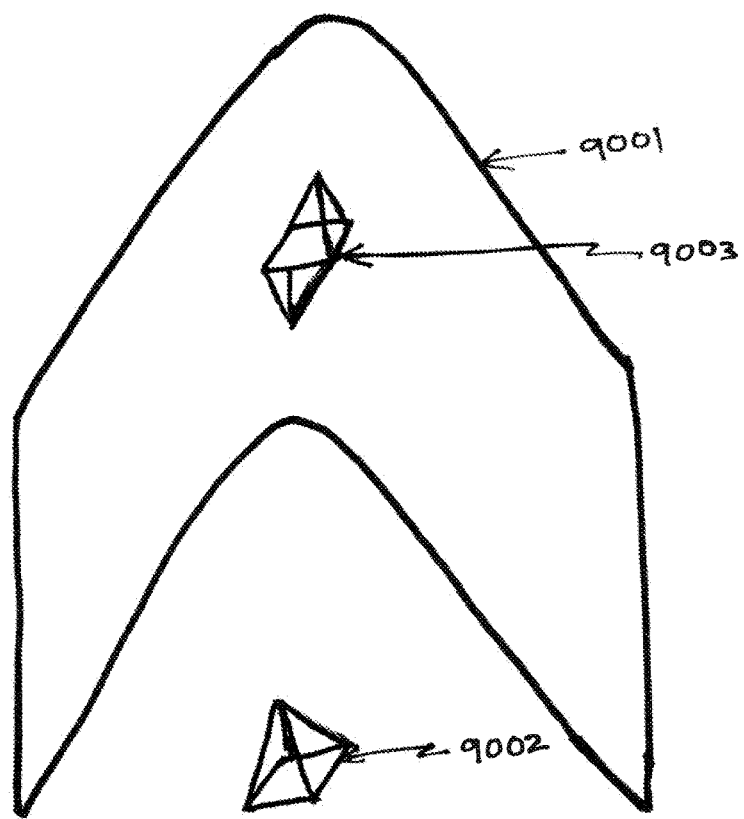
FIG. 9a illustrates a foldable free space "pop-out" & "sink-in" hologram display.
Figure 9B:
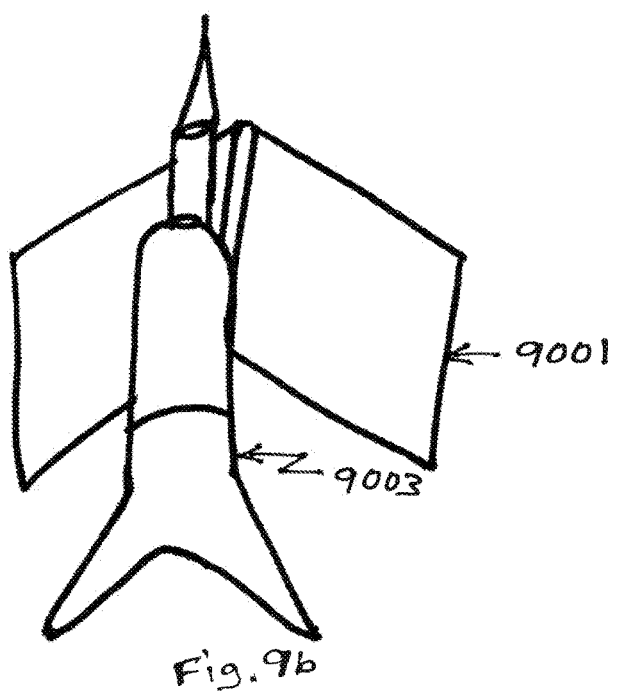
FIG. 9b illustrates a foldable free space "pop-out" & "sink-in" hologram display with a hinge at the middle of the screen.
Figure 10:
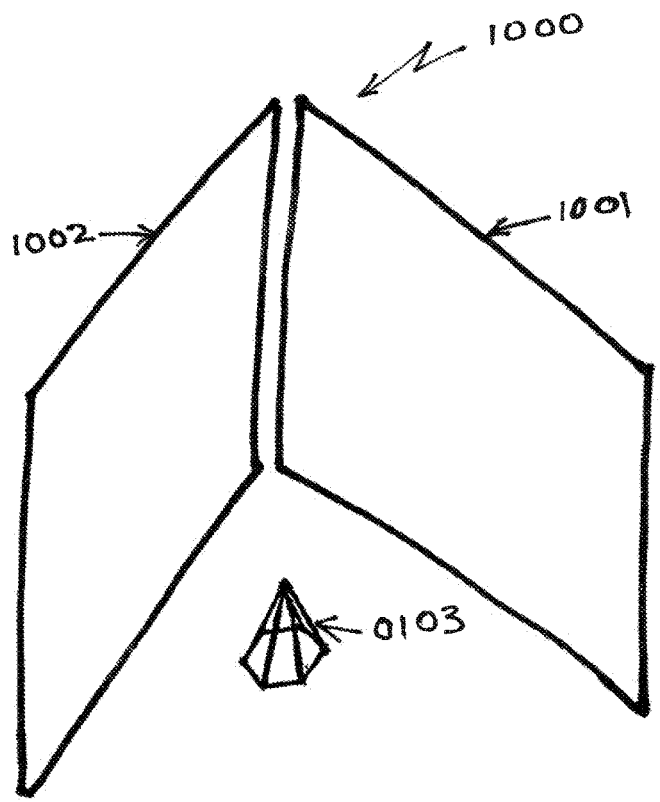
FIG. 10 illustrates a foldable free space "pop-out" & "sink-in" hologram display with a hinge at the middle of the screen.
Figure 11:
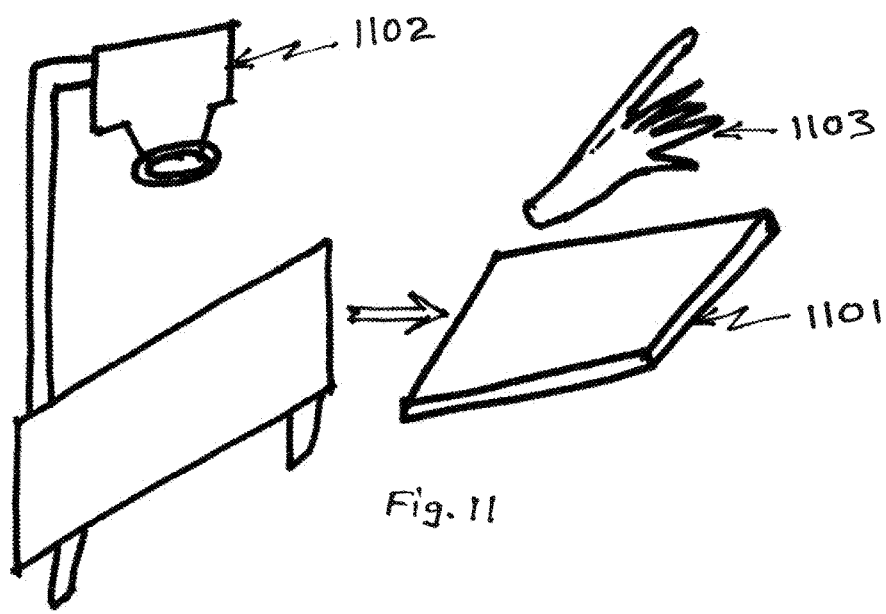
FIG. 11 illustrates a free space "pop-out" & "sink-in" hologram display panel being used in healthcare equipment.
Figure 12:
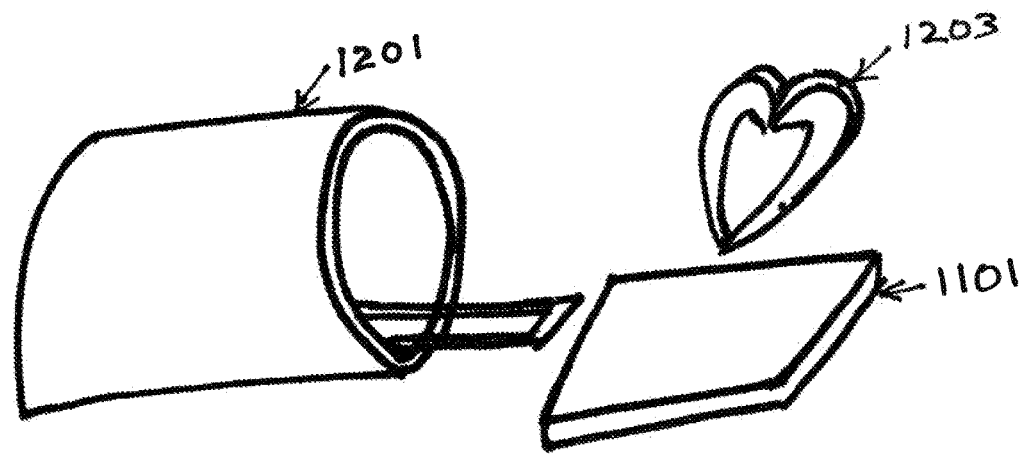
FIG. 12 illustrates a free space "pop-out" & "sink-in" hologram display panel being used in healthcare equipment such as MRI and CAT scan machines.
Figure 13:
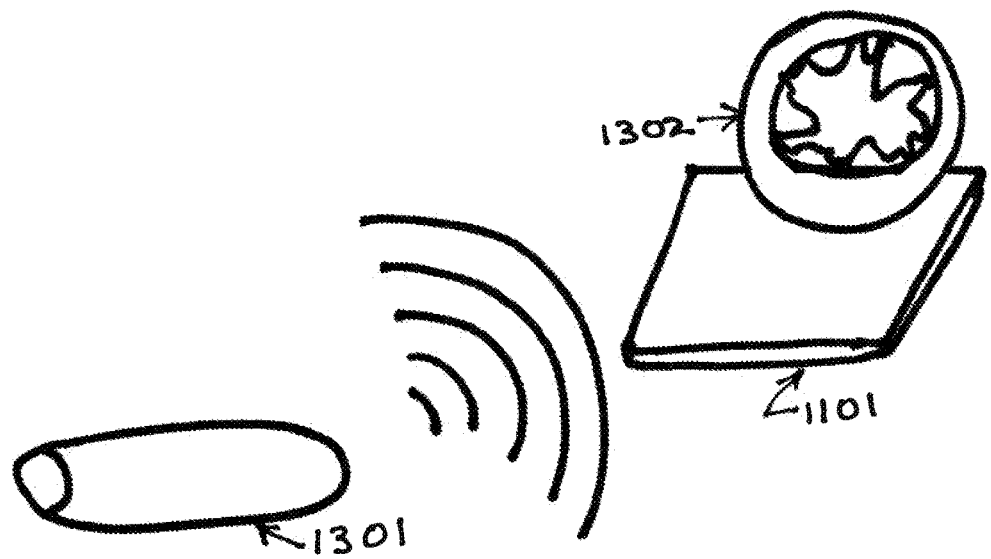
FIG. 13 illustrates the images captured using an endoscopic capsules being viewed on the free space "pop-out" & "sink-in" hologram display device.
Figure 14:
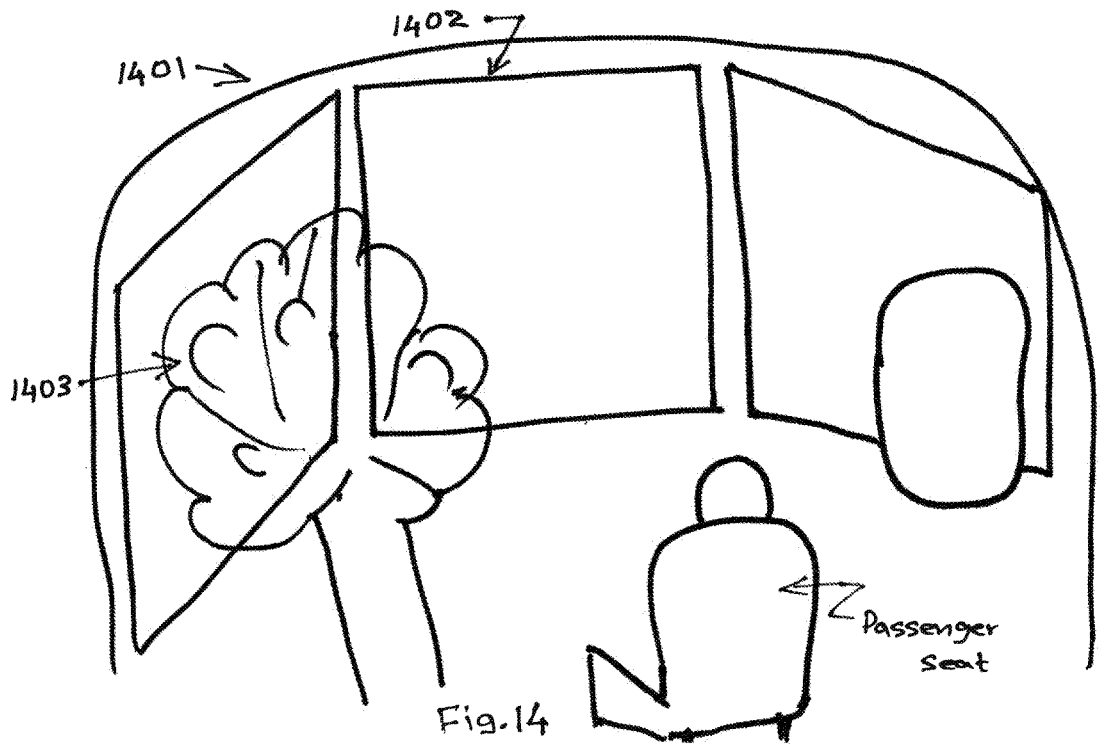
FIG. 14 illustrates the free space "pop-out" & "sink-in" hologram display screens being used to create different multiple environments inside an aircraft cabin or inside the car cabin or inside the house or inside a space craft or inside a vehicle as examples.
Figure 15:
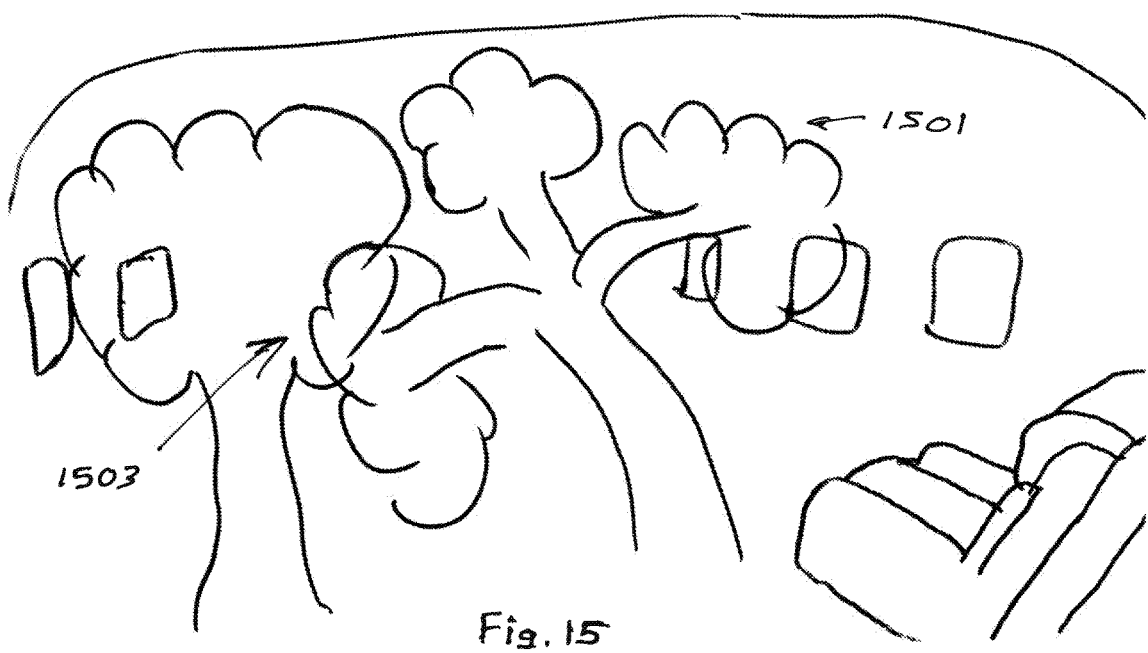
FIG. 15 illustrates the free space "pop-out" & "sink-in" hologram display screen made with a flexible screen or rigid screen. The flexible free space "pop-out" & "sink-in" hologram screen is used as a sticker or a wall paper on the inner walls or partitions of the aircraft cabin or in any other vehicle cabin or the building.
Figure 16:
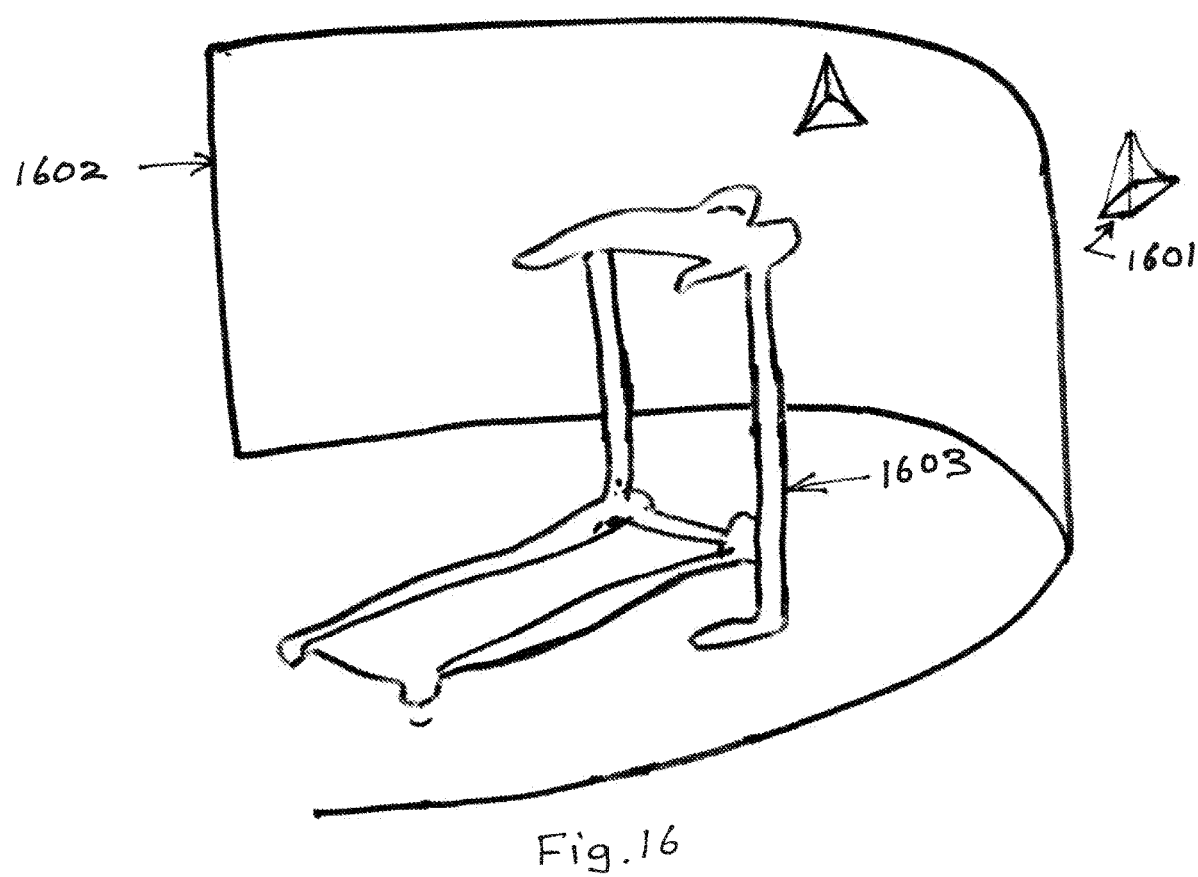
FIG. 16 illustrates the free space "pop-out" & "sink-in" hologram display panels being used to create different multiple environments inside a Gymnasium, stadium, surrounding an exercise machine thereby creating a virtual 3D environment.
Figure 17:
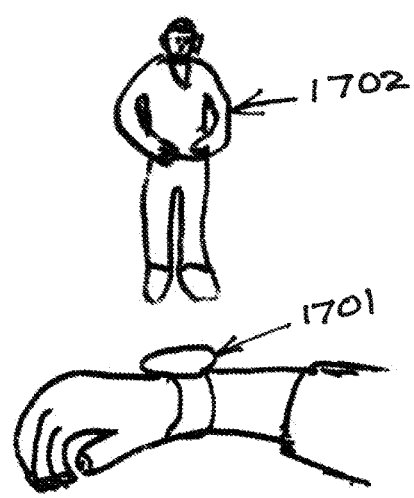
FIG. 17 illustrates the free space hologram display panel being used for a smart wrist watch which has phone and wireless broad band functions.
Figure 18:
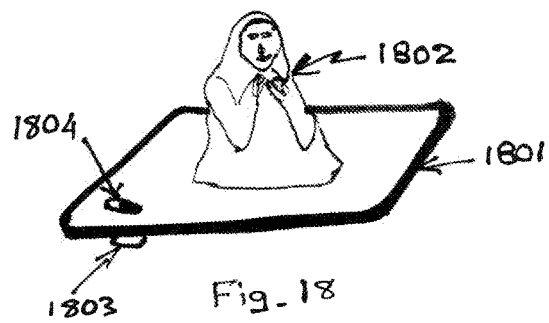
FIG. 18 illustrates the free space hologram display screen being used in a mobile device for use in video conferencing such that individuals' images are seen in free space holograms on top of the free space hologram screen.
Figure 19:
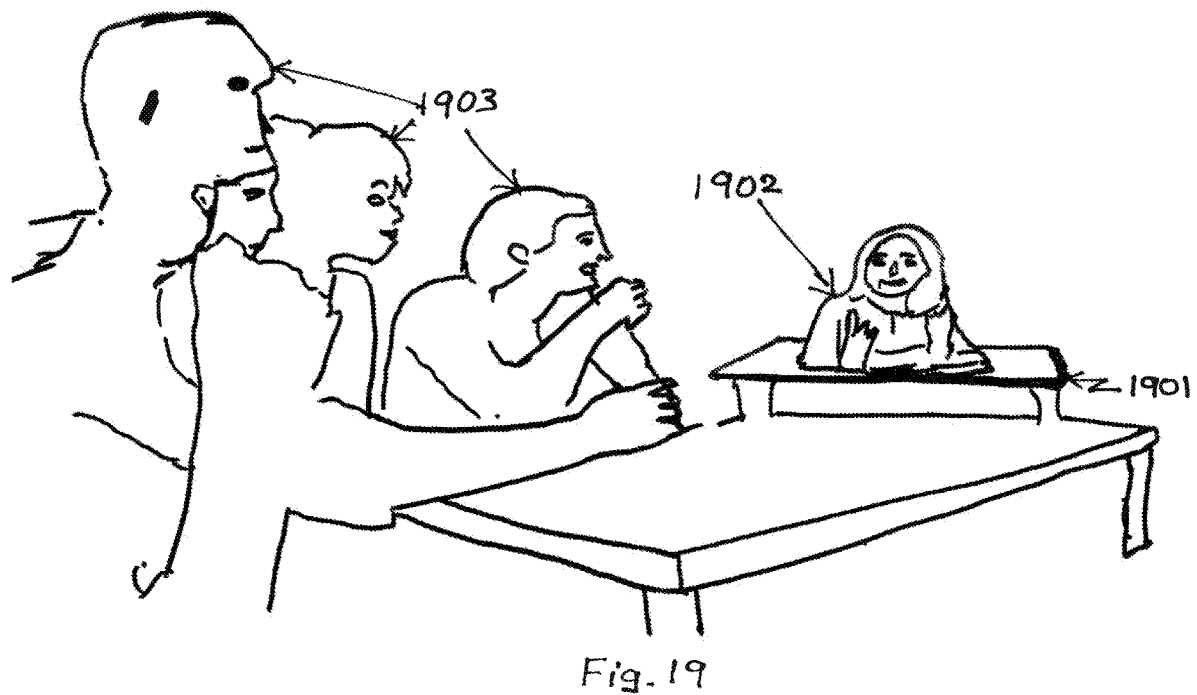
FIG. 19 illustrates the free space hologram display screen being used in a television, allowing the viewer to watch any mundane television programme such as sports or news in breath taking "pop-out" & "sink-in" holographic form.
Figure 20:
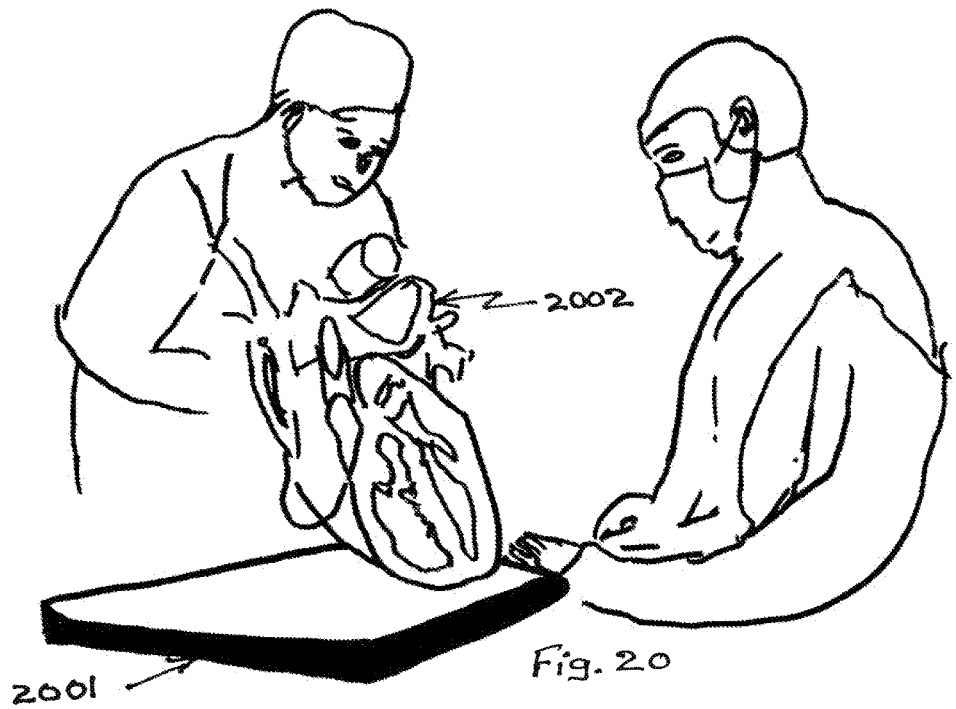
FIG. 20 illustrates the free space hologram display screen being used in medical equipment such as X-ray images, Computerized Axial Tomography (CAT) scan images, Magnetic Resonance imaging (MRI) scan images, ultra sound scan images, images acquired by Endoscope, images acquired by Endoscopic capsules.

In the following description, numerous specific details are set forth in order to provide a thorough understanding of various illustrative embodiments of the invention. It will be understood, however, to one skilled in the art, that embodiments of the present invention may be practiced without some or all of these specific details. In other instances, well known process operations have not been described in order not to unnecessarily obscure pertinent aspects of embodiments being described.

In one embodiment, a free space "pop-out" & "sink-in" hologram (0403) is seen or created on top of the flexible or rigid displays but not limited to the following: Liquid Crystal Display (LCD) or various types of Light Emitting Diode display (LED) or various types of Organic Light Emitting Diode display such as OLED, AMOLED but not limited for these, Thin Film Transistor (TFT), Cathode Ray Tube (CRT), Electronic Paper display, Digital Paper display or any type of pixelated display, pixelated images & photos, pixelated video, illuminated photo or illuminated picture or similar display panel (0401) having multi level structure (0402) built on it, but not limited to these display panel types. The present invention details a method and a device where the free space "pop-out" & "sink-in" hologram can be viewed from all directions and can walkthrough, or put the hand through the free space "pop-out" & "sink-in" hologram (0403). Further, the free space "pop-out" & "sink-in" hologram disclosed herein does not use any special medium such as smoke, mirrors, reflective screens or wearables such as headgear & special glasses. A few specific features and structures (0402) are placed on the display panel (0401) in order to guide light in such a manner to obtain the free space "pop-out" & "sink-in" hologram on the free space "pop-out" & "sink-in" hologram display panel (0300).

In one embodiment, the Free space "pop-out" & "sink-in" hologram panel (0300) which is capable of displaying free space "pop-out" & "sink-in" holograms, "pop out" or "sink in" 3D Augmented reality (AR), Virtual reality (VR) & mixed (MR) reality contains one or more different stacks (0402) of material having different optical properties and features, where in a Liquid Crystal Display (LCD) based or any type of Light Emitting Diode (LED) based or light based or Cathode Ray Tube (CRT) display based or electronic paper based or digital paper display or pixelated based display or any type of pixelated based display or pixelated images & photos based or pixelated video based or illuminated picture based or illuminated photo based free space "pop-out" & "sink-in" hologram display (0300), the special features with special material having special properties are built on top of the display. Typical multi-layered (0402) structure built on the display (0401) generates the hologram (0403) in free space. The multi layer structure may contains one or a combination of the following: optical focusing layer & structure, optical lens array, optical refractive layer & structure, optical diffraction layer, Optical guide layer and structure, optical spacer layer, diverging optics layer, converging optics layer, lenticular optics layer, optical total internal reflection structure layer, optical total internal reflection layer, adhesive layers, optical coupling layers, optical adhesive coupling layers, electro magnetic or electro static actuator for fine tuning of hologram, hydraulic or pneumatic actuator for fine tuning of hologram, single or multiple cameras for eye tracking, Display with an array of pixels, Backlight for display illumination, Backlight illumination with quantum dots, Colour filter and filter array.

In one embodiment, the Free space hologram display which is capable of displaying free space "pop-out" & "sink-in" holograms, "pop out" or "sink in" 3D Augmented reality (AR), Virtual reality (VR) & mixed (MR) reality contains one or more different layers of material having different optical properties and features, where in a Liquid Crystal Display (LCD) based or any type of Light Emitting Diode (LED) based or light based or Cathode Ray Tube (CRT) based display or illuminated picture based or illuminated photo based free space "pop-out" & "sink-in" hologram display (0300) has the special material with special properties and features are built on top of the display. Typical multi-layered structure (0402) built on the display generates the hologram in free space (0403). The multi layer structure (0402) contains one or more of the following: combined array of lenses and mirrors, array of prisms, array of lenses, array of mirrors, array of lenticules, array of lenticular lenses, array of convex lenses, array of concave lenses, array of diverging lenses, array of converging lenses, array of multi faced structures, array of multi faced lenses, array of multi faced mirrors, array of diverging optics, array of converging optics, array of lenticular optics, array of actuators, array of electromagnetic filters, array of colour filters, array of polarisers, array of optical filters, array of mirrors, array of hydrophilic areas, array of optical total internal reflecting structures, array of hydrophobic areas, array of both a combination of hydrophilic (6001) and hydrophobic (6002) areas, array of liquid lenses of various shapes and kinds, array of electromagnetic inductors. The dimensions of each of the above can vary between a few nanometre to a few millimetre or a few centimetre.

In one embodiment, the free space hologram display (0300) can be used with single or multiple mirrors (5001) in order to view multiple holograms along with the free space hologram (5002). The mirrors are placed at various angles to the free space "pop-out" & "sink-in" hologram display screen (0300), but still forming the free space "pop-out" & "sink-in" hologram (5002) in front of the mirror, so that the observer can touch through the free space hologram In one embodiment, liquid lenses (6003) or lens arrays are formed on the surface of the display screen (6000) in order to create the free space hologram (6004). The liquid lenses are created by patterning hydrophilic (6005) and hydrophobic (6006) areas on the surface of the display and applying the liquid onto this patterned surface, thereby creating lenses on the hydrophilic areas. The liquid lenses are self-formed on the hydrophilic areas, when liquid is smeared over the surface which has patterned hydrophilic and hydrophobic areas.

In one embodiment, the optical patterns or array of optical lenses or material or structures are made on top of the display screen (7000) in multiple directional patterns in order to make full round free space "pop-out" & "sink-in" hologram where the observer can view the front, back, two sides' views by walking around the free space hologram. For an example, the display screen (7000) may be divided into four triangular regions and the material used and the structural pattern (7001) in each region is specifically designed for that particular region.

In one embodiment, one or more of the array of structures (8001) or array of lenses or array of actuators or optical & electromagnetic/electrostatic components may be moved with respect to the display screen (8003) in order to optimise the performance and quality of the free space "pop-out" & "sink-in" hologram display panel (8000), by means of an electrostatic actuator (8002) or electromagnetic actuator.

In one embodiment, a foldable free space "pop-out" & "sink-in" hologram display (9001) can be used as a foldable book, foldable tablet, foldable monitor, foldable television, foldable phone, where when the display is folded it looks as if a closed book and when it is opened it can be a free space "pop-out" & "sink-in" hologram (9002) generating book or a free space "pop-out" & "sink-in" hologram generating tablet or a free space "pop-out" & "sink-in" hologram generating monitor or a free space "pop-out" & "sink-in" hologram generating television or a free space "pop-out" & "sink-in" hologram generating phone. Here, when the folded display is opened, the free space "pop-out" & "sink-in" hologram will pop out. All these can display sink-in or pop out free space "pop-out" & "sink-in" holograms (9003) and free space "pop-out" & "sink-in" hologram Augmented reality (AR) or Virtual reality (VR) or mixed (MR) reality.

In one embodiment, two or more free space "pop-out" & "sink-in" hologram display screens (1001) (1002) may be joined together with hinges to create a foldable free space hologram display (1000). This foldable hologram display can be used as a hologram book, foldable tablet, foldable monitor, foldable television, foldable phone, where when the display is folded it looks as if a closed book and when it is opened it can be a hologram generating book or a hologram generating tablet or hologram generating monitor or hologram generating television or hologram generating phone. Here, when the folded display is opened, the free space "pop-out" & "sink-in" hologram (1003) will pop out.

In one embodiment, the free space "pop-out" & "sink-in" hologram display panel (1101) disclosed herein is used for mobile phones, television, computer monitors and the display used in health care equipment such as x-ray machines (1102), Computerized Axial Tomography (CAT) scan machines (1201), Magnetic Resonance Imaging (MRI) scanner machines (1201), ultra sound scanner machines, Endoscopes, Endoscopic capsules (1301) to view the scanned images (1103), (1203), (1302) in free space "pop-out" & "sink-in" hologram. For example, when a fetal scan is performed on a pregnant mother in order to check the health of the fetus, the fetus is seen as a free space "pop-out" & "sink-in" hologram where the fetus can be seen above the free space "pop-out" & "sink-in" hologram display panel used with the scanner equipment and the physician can make a precise evaluation on the fetus. Further, by using a phone or a tablet or a suitable device equipped with the free space "pop-out" & "sink-in" hologram display panel, the parents of the fetus can do a "virtual cuddle" of the fetus by using the free space "pop-out" & "sink-in" hologram of the fetus. The endoscopic capsule while inside the human body is used to capture video or still images and display the captured multimedia content on the free space "pop-out" & "sink-in" hologram display device.

In one embodiment, the free space "pop-out" & "sink-in" hologram display panel is connected to a device or component where specially processed video signal or still image is generated and delivered to the input of the hologram display. The device or the component may have wi-fi, Bluetooth, 2G, 3G, 4G, 5G or other communication means, GPS capability and other multiple digital and analogue functions and operations.

In one embodiment, the free space "pop-out" & "sink-in" hologram display screens (1402) are used to create different multiple environments inside an aircraft cabin (1401) or inside the car cabin or inside the house or inside a space craft or inside a vehicle, and inside or outside of an exhibition booth for displaying thousands or millions of products using the free space "pop-out" & "sink-in" hologram (1403), display of precious & luxury goods, but not limited to these. For example, the aircraft passenger can bring his own preferred environment content saved or recorded into a digital or analogue memory such as a memory card, hard disk, thumb drive, etc. For example, but not limited to the following, the free space pop out and sink-in hologram is used to simulate and create an environment such as being in a jungle (1403) (1503), seashore, view a movie in free space "pop-out" & "sink-in" hologram or whatever the audience/passenger wish to have. The free space "pop-out" & "sink-in" hologram device can be loaded with 3D models created with CAD software and these models can be used to generate free space "pop-out" & "sink-in" holograms. The environment can be created in all areas and directions which the audience can see. The free space "pop-out" & "sink-in" hologram display screen (1402) can be made with a flexible screen or rigid screen. The flexible free space "pop-out" & "sink-in" hologram screen (1501) is used as a sticker or a wall paper on the inner walls or partitions of the aircraft cabin or in any other vehicle cabin or the building.

In one embodiment, the free space "pop-out" & "sink-in" hologram display panels are (1602) used to create different multiple environments (1601) inside a Gymnasium, stadium, surrounding an exercise machine (1603) creating virtual "pop-out" & "sink-in" environment such as for example a "pop-out" & "sink-in" hologram jungle where the exercise machine is immersed in the free space "pop-out" & "sink-in" hologram, but not limited to these. For example, but not limited to the following, the free space pop out and sink-in hologram is used to simulate and create an environment such as being in a jungle, seashore, or whatever the audience wish to have. The environment can be created in all areas and directions which the audience can see.

In one embodiment, the user of the free space "pop-out" & "sink-in" hologram display device can create his own free space "pop-out" & "sink-in" hologram by making a drawing with the software provided in the hologram device and then applying the necessary transforms and transformations to the drawings and then displaying the free space "pop-out" & "sink-in" hologram of the drawing on the free space "pop-out" & "sink-in" hologram display device.

In one embodiment, the free space hologram display panel is used for a smart wrist watch (1701) which has phone and wireless broad band functions. When receiving a phone call or communicating using this hologram smart watch, a free space hologram can be seen of the other caller (1702).

For example, it may be seen as if the other caller was standing or sitting on the smart hologram watch which has the phone facility (1701).

In one embodiment, the free space "pop-out" & "sink-in" hologram (1802) can be turned ON or turned OFF by means of a 4-way hardware switch (1803) or a 4-way soft switch (1804) whereby the display is toggled between 2D mode, sink-in mode, pop-out mode and free space "pop-out" & "sink-in" 3D hologram mode. when the hologram display is operated in 2D mode, the display clarity is maintained in such a way that very fine text or features displayed on the display can be seen very clearly and much clearer than the iPhone 11 Pro max display or any other mobile display available at present. When the hologram display is operated in 2D or "pop-out" & "sink-in" modes, the display clarity is maintained in such a way that very fine text displayed on the display can be seen very clearly. In 3D mode, free space "pop-out" & "sink-in" hologram mode and 2D mode, it can operate in full colour and in High definition (HD) or Ultra High Definition (UHD) or 4K or 8K or any other higher or lower resolution and not limited to these resolutions.

In one embodiment, the free space hologram display screen (1801) is used in a mobile device for use in video conferencing such that individuals' images are seen in free space holograms (1802), on top of the free space hologram screen and the free space "pop-out" & "sink-in" hologram is used in virtual personnel assistants such as APPLE Inc.'s "Siri" voice assistant, Google Google Assistant, Amazon Inc.'s Alexa voice assistant, etc, but not limited to these, where it shows a person (1802) in free space "pop-out" & "sink-in" hologram over or on the mobile device or hologram device interactively talking with the user of the device, to make the experience with the virtual personnel assistant more realistic.

In one embodiment, the free space hologram display screen (1801) is used as a GPS navigation equipment so that users are able to clearly visualise the environment they will be heading to, and for entertainment such as gaming, watching videos and sports, popping up of a free space "pop-out" & "sink-in" hologram human FIG. 1802) when using voice assistant such as "Siri" in Apple devices, just to name a few.

In one embodiment, the free space hologram display screen is used in a television (1901), allowing the viewer to watch any mundane television programme such as sports or news in breath taking "pop-out" & "sink-in" holographic form. The television can be either placed vertically or horizontally and can be rotated to make it to be in a landscape position or portrait position, thereby enabling multiple viewers (1903) to view the free space "pop-out" & "sink-in" hologram (1902) from multiple directions and multiple modes.

In one embodiment, the free space hologram display screen (2001) is used in medical equipment such as X-ray images, Computerized Axial Tomography (CAT) scan images, Magnetic Resonance Imaging (MRI) scan images, ultra sound scan images, images acquired by Endoscope, images acquired by Endoscopic capsules, just to name a few but not limited to these. This allows these images to be seen in holographic form (2002) and hence facilitates viewing and analysis by multiple personnel from 360° around the hologram.

In one embodiment, the free space hologram display screen (2101) is used in educational took such as an AR (Augmented Reality)/VR (Virtual Reality)/MR (Mixed Reality) training tool or device (2102) for professionals and students. This works by hovering the device with the "pop-out" & "sink-in" hologram display above a specific text or image (2103) to activate the AR/VR function on the device (2102) so that specific visuals of how a machine works (2105), how a science experiment is carried out or a visual representation of what a text in a text book describes about may be seen in a holographic form to enhance learning. This use may prove especially important in the education industry where for example, medical staff will be able to view entire systems in the human body in a "pop-out" & "sink-in" holographic form, simply by hovering the free space "pop-out" & "sink-in" hologram device with the camera turned ON over their textbooks or notes, allowing them to more easily visualise what needs to be done in medical procedures such as surgeries. Similarly, the free space "pop-out" & "sink-in" hologram display used for the free space hologram AR/VR/MR device (2012) can be either an active free space "pop-out" & "sink-in" hologram display when electric power is used or passive free space "pop-out" & "sink-in" hologram display where electric power is not used. In this invention the free space "pop-out" & "sink-in" hologram AR/VR/MR device (2102) equipped with the free space "pop-out" & "sink-in" hologram display panel (2101) can be used in training manuals (2106) for viewing, for example an aircraft engine (2103) in "pop-out" & "sink-in" holographic space can be viewed and it's possible to visualize its parts in free space "pop-out" & "sink-in" holographic space (2105). When the AR, VR, MR device's camera is used to scan a book and when the camera focus on a particular diagram/photo/video, the AR, VR or MR will automatically play the related content on the free space "pop-out" & "sink-in" hologram.

In one embodiment, free space "pop-out" & "sink-in" hologram display screen/device (2201) is used in webinars, web based virtual meetings (2200), virtual tours with free space "pop-out" & "sink-in" holograms for marketing, distant learning, e-learning, educational seminars, training seminars, business meetings (2200), medical & collaboration meetings, tele medicine and many more uses and applications where the people & objects can be seen in free space "pop-out" & "sink-in" holograms (2202) as if the living person or objects are sitting or standing on the display screen (2201), thereby creating a virtual 3D environment (2200) which brings the participants of virtual meetings to feel to be very much natural to the person (2203) conducting or participating in the virtual meeting.

In one embodiment, the free space "pop-out" & "sink-in" hologram display device equipped with free space "pop-out" & "sink-in" hologram display screen (2301) is used in the fashion industry, where holographic images of various clothing (2302) items from hats and shoes to T-Shirts and dresses can be displayed to show the exact dimensions of the article of clothing, allowing the buyer (2303) to visualise exactly how they would look when dressed in it, thus providing a virtual 'fit-on' experience. This is especially advantageous when it comes to online shopping where it is very difficult to visualise how one may look in a certain article of clothing. With the free space hologram display device, this issue will be tackled. Here, a photograph of the person can be captured with a camera and the persons photograph can be converted to a free space hologram and the clothing which needs to be checked out which is also in hologram form (2302) can be superimposed on the person's photograph (2303) in order to view how good or bad the particular clothing will look on the person. Life size free space hologram of clothes (2304) can be formed on a free space hologram device (2301) which is placed horizontally or flat on the floor and generating the hologram to be vertical. In order to do a virtual fit on of clothes, a person (2305) can walk into the hologram and check how the clothes in the hologram will look like on him by another person. The dress designers, can use the free space hologram (2304) to design dresses so that special dresses can be done a virtual try-on before even sewing the dresses, similarly Design engineers can use the free space "pop-out" & "sink-in" hologram devices with CAD (Computer Aided Design) tools to generate and view live size free space "pop-out" & "sink-in" holograms (2304) to check their designs of cars, engines, buildings, machines, equipment, consumer items, industrial goods, to list a few but not limited to these.

In one embodiment, a movie can be watched in free space "pop-out" & "sink-in" hologram (2306) by having a large size free space hologram device (2301) equipped with a free space "pop-out" & "sink-in" hologram screen placed horizontally on the floor and generating the movie in hologram (2306) to be vertical. For example a hologram house (2306) is created by free space "pop-out" & "sink-in" hologram device screen and then, the audience (2307) can walk into the hologram house, creating the first walk-through movie experience.

In one embodiment, the free space "pop-out" & "sink-in" hologram Augmented Reality (AR) device or a free space "pop-out" & "sink-in" hologram Virtual Reality (VR) device or a free space "pop-out" & "sink-in" hologram Mixed Reality (MR) device is realized by attaching a free space "pop-out" & "sink-in" hologram enabling screen on top of the AR device or AR hardware, VR device or VR hardware, MR device or MR hardware or including any other 3D enabled 3D screen onto the AR device. The free space "pop-out" & "sink-in" hologram enabling screen or 3D enabling screen is not limited to LCD, Light Emitting Diode based or Liquid Crystal Display (LCD) or various types of Light Emitting Diode display (LED) or various types of Organic Light Emitting Diode display such as OLED, AMO-LED but not limited for these, Thin Film Transistor (TFT), Cathode Ray Tube (CRT), Electronic Paper display, Digital Paper display or illuminated photo or illuminated picture or similar display panel having multi level structure built on it or attached onto it, but not limited to these display panel types or only an attachment on top of the existing screens. The multimedia content artificially introduced into the image or live video captured by the camera of the free space "pop-out" & "sink-in" hologram AR, VR or MR device is processed in such a way that the artificially introduced content be viewed to be as if to be coming out of the "pop-out" & "sink-in" display screen or the content to be sink inside the display screen. The free space "pop-out" & "sink-in" hologram AR is created by a combination of 2D, 3D & hologram optical hardware and multimedia content. The 3D viewing may be done by means of both using special eye ware or glasses or even without using special eye ware or glasses.

In one embodiment, a reflective plate, reflective surface or a reflective mirror (5001) is placed at an angle to the free space "pop-out" & "sink-in" display panel, thereby enhancing or multiplying the free space "pop-out" & "sink-in" holograms (5002) which are displayed on top of free space "pop-out" & "sink-in" hologram display panel (0300).

Figure 21A:
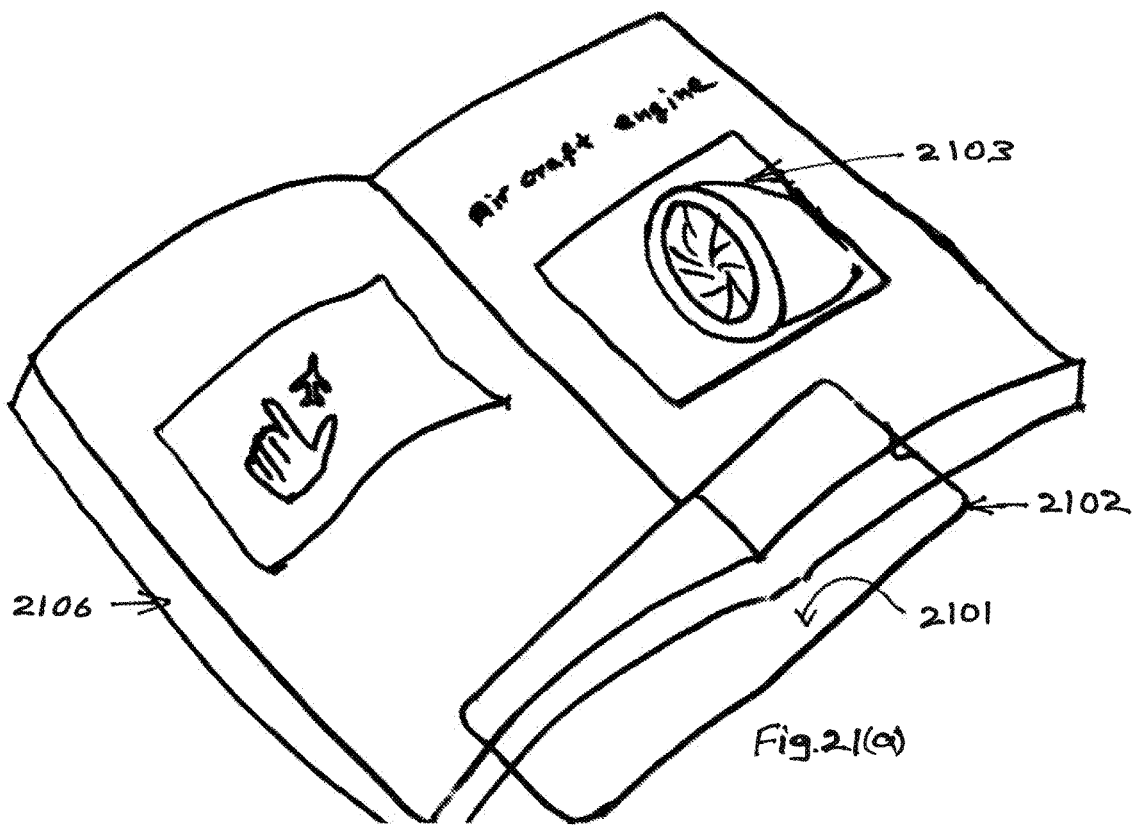
FIG. 21a illustrates the free space hologram display screen being used in educational tools such as an AR (Augmented Reality)/VR (Virtual Reality)/MR (Mixed Reality) training tool or device for professionals and students.
Figure 21B:
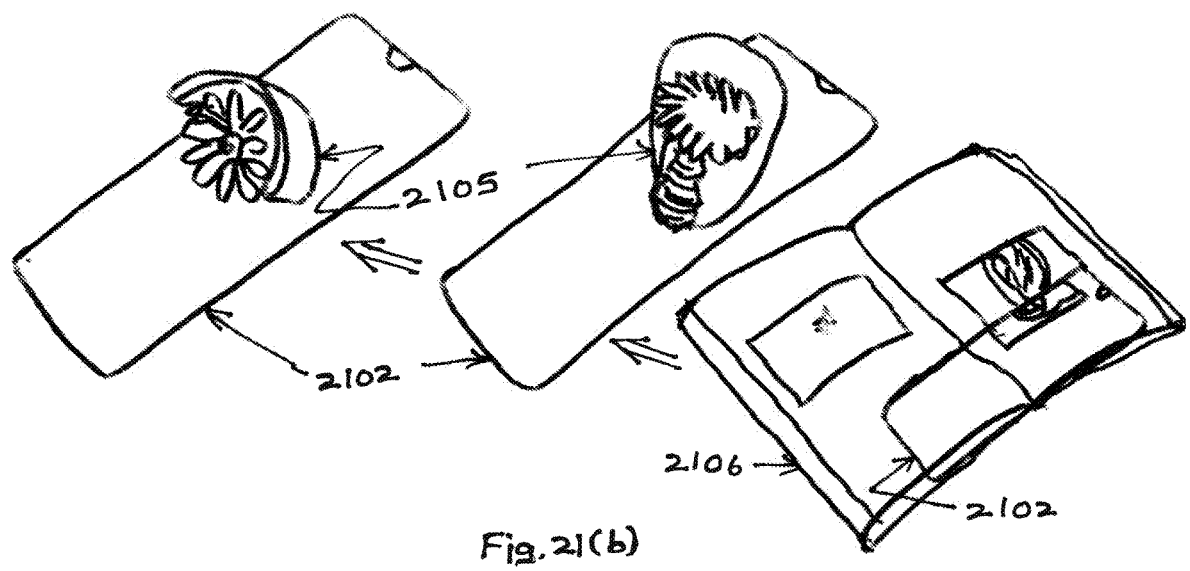
FIG. 21b illustrates the free space hologram display screen being used in educational took such as an AR (Augmented Reality)/VR (Virtual Reality)/MR (Mixed Reality) training tool or device for professionals and students.
Figure 22:
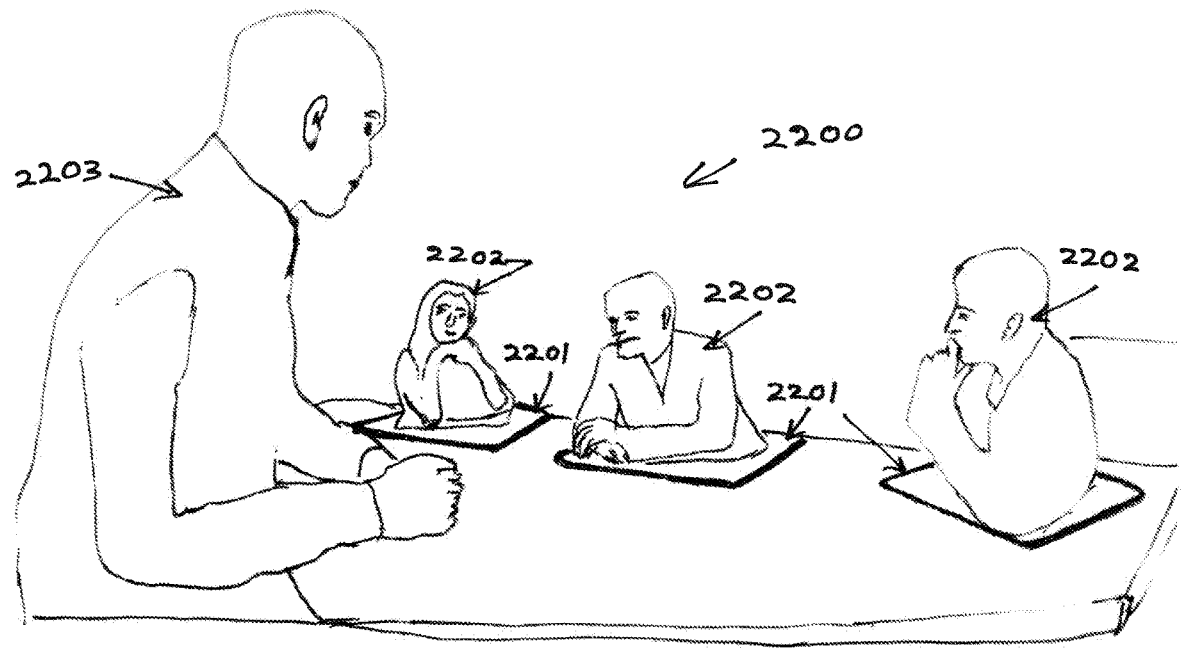
FIG. 22 illustrates the free space "pop out" & "sink-in" hologram display screen/device being used in webinars, web based virtual meetings, virtual tours with free space "pop-out" & "sink-in" holograms for marketing, distant learning, e-learning, educational seminars, training seminars, business meetings, medical & collaboration meetings, tele medicine.
Figure 23A:
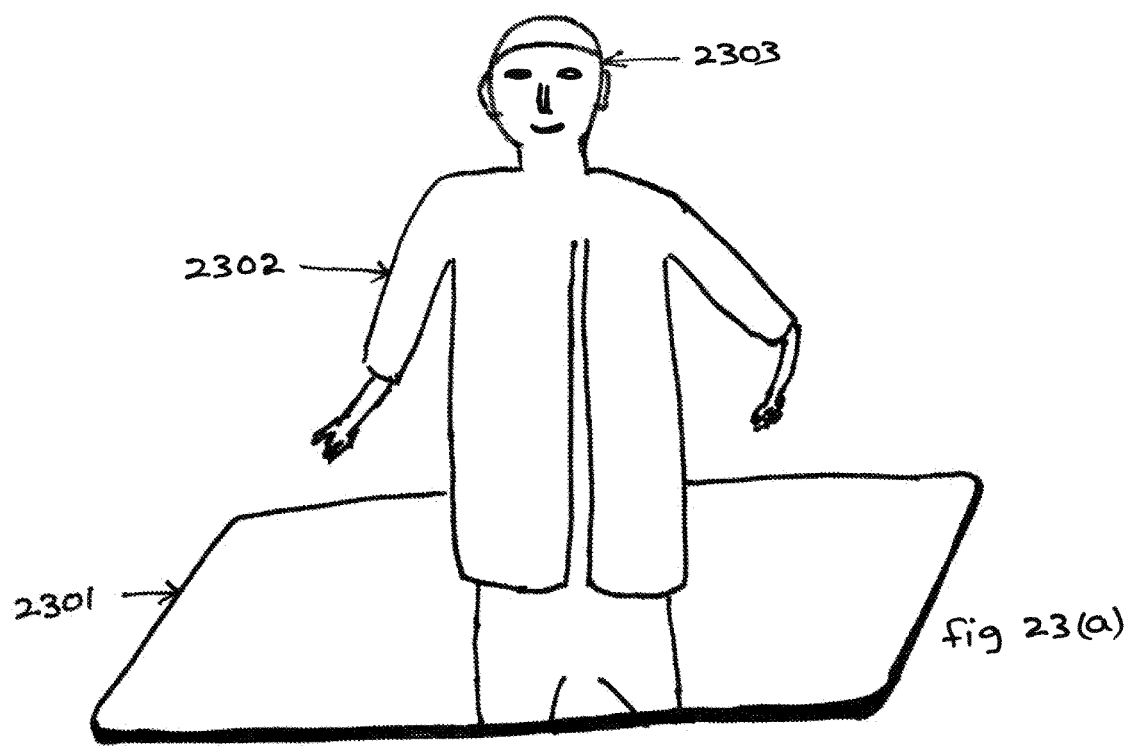
FIG. 23a illustrates the free space "pop-out" & "sink-in" hologram display device equipped with free space "pop-out" & "sink-in" hologram display screen being used in the fashion industry, where holographic images of various clothing can be displayed as a hologram.
Figure 23B:
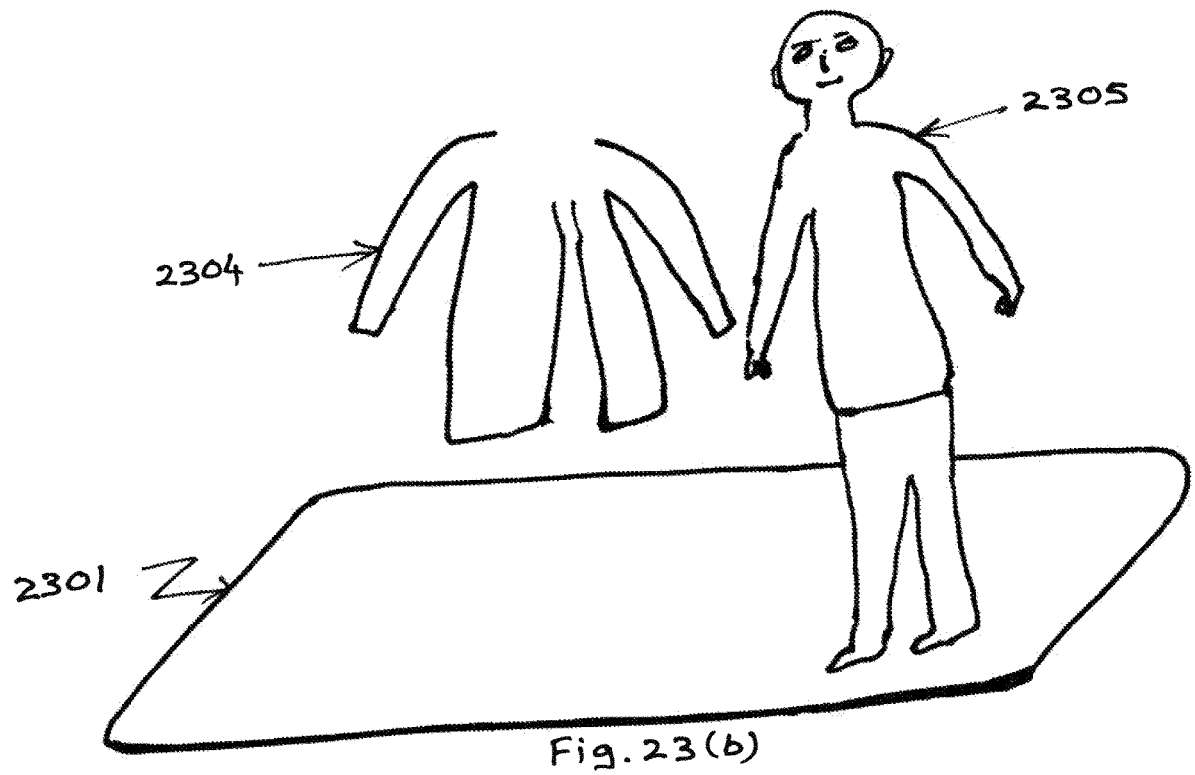
FIG. 23b illustrates A life size free space hologram of clothes formed on a free space hologram device which is placed horizontally or flat on the floor and generating the hologram to be vertical. In order to do a virtual fit on of clothes, a person can walk into the hologram and check how the clothes in the hologram will look like on him by another person.
Figure 23C:
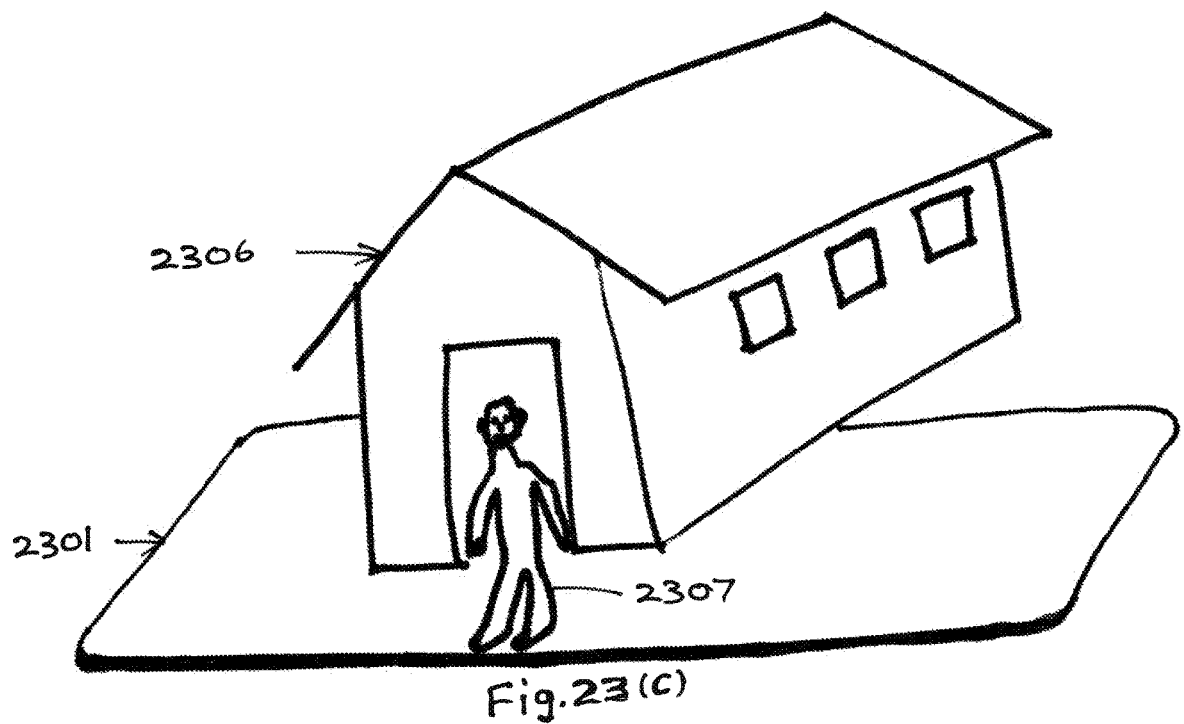
FIG. 23c illustrates the audience can walk into the objects in movie such as a free space "pop-out" & "sink-in" hologram house, creating the first walk-through movie experience using free space "pop-out" & "sink-in" hologram.
Figure 24A:
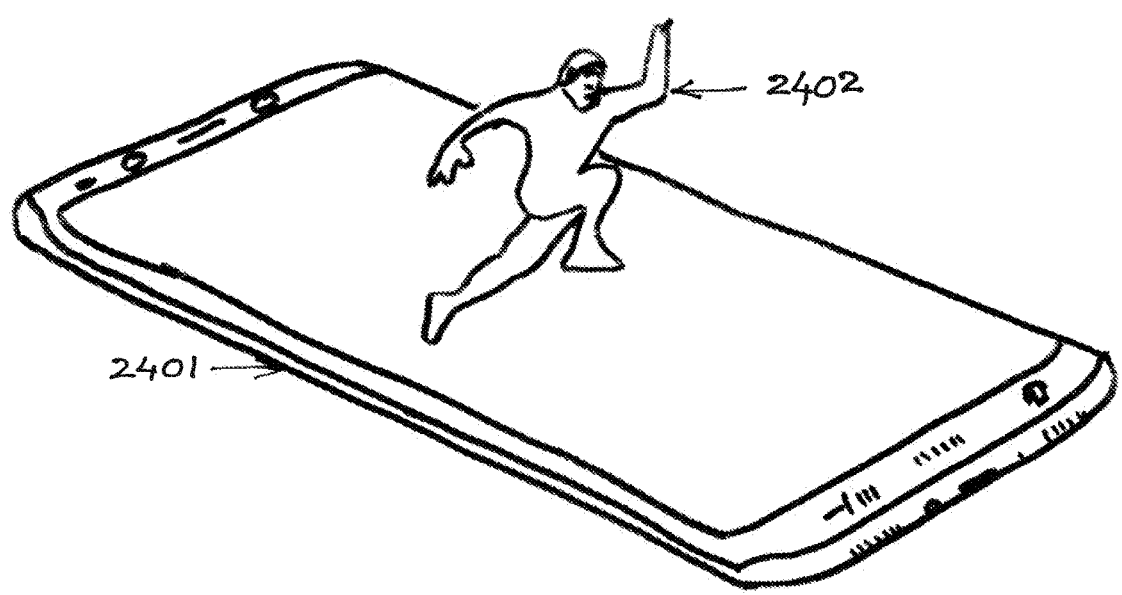
FIG. 24a illustrates a multimedia device or an image & video display device or a component having a visual free space "pop-out" & "sink-in" hologram display with a combination of free space "pop-out" & "sink-in" hologram pop-out and sink-in free space "pop-out" & "sink-in" hologram effects on Augmented reality, virtual reality and mixed.
Figure 24B:
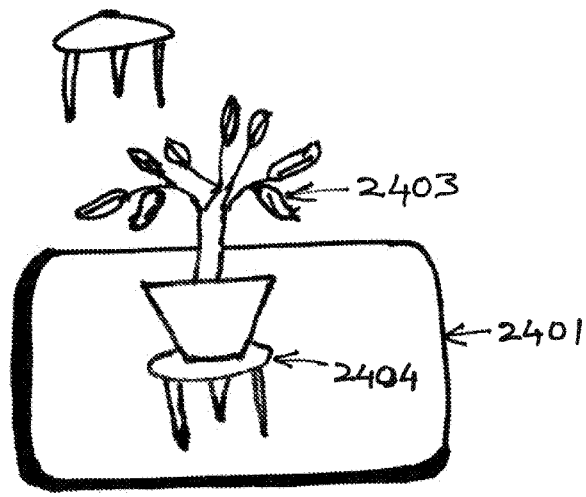
FIG. 24b illustrates new virtual objects being inserted into the live image captured by the camera of the AR, VR, MR device where the new object and the live image are both displayed in pop-out & sink-in hologram
Figure 25:
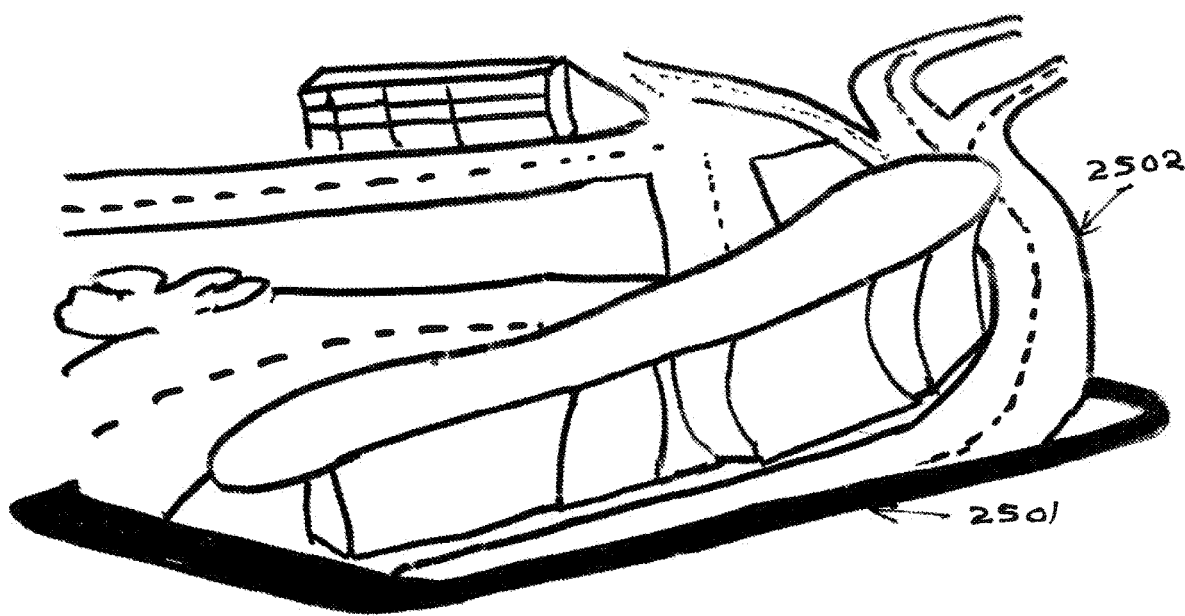
FIG. 25 illustrates the free space "pop-out" & "sink-in" hologram AR device being used for viewing street view maps.
Figure 26:
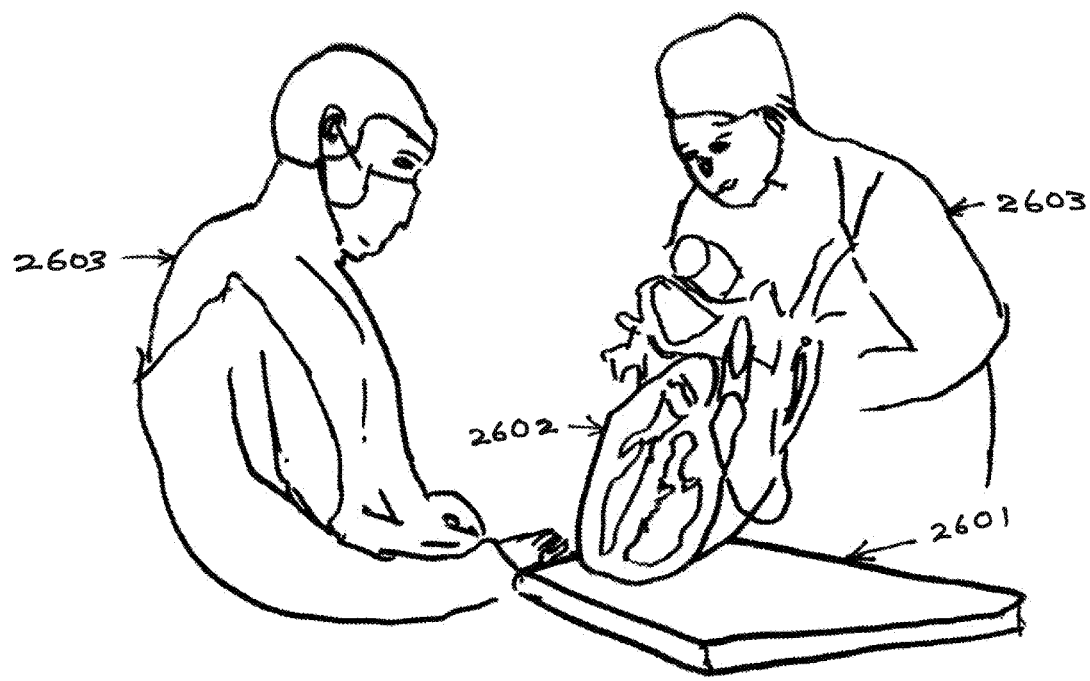
FIG. 26 illustrates the free space "pop-out" & "sink-in" hologram device being used for simultaneous viewing of "pop out" or "sink in" 3D Augmented reality (AR) or Virtual reality (VR) or mixed (MR) reality by multiple people, with a single device.

In one embodiment, a multimedia device (2401) or an image & video display device or a component having a visual display with a combination of one or more of the following enables the free space "pop-out" & "sink-in" hologram (2402) pop-out and sink-in free space "pop-out" & "sink-in" hologram effects on Augmented reality, virtual reality and mixed device may have the following:

camera having a human eye like lens (2802) for capturing "pop-out" & "sink-in" hologram capable images A camera lens which mimics the human eye by changing it's lens aperture according to the light intensity as the pupil of the human eye (3001) and focus & capture "pop-out" & "sink-in" images disclosed herein.

have software to operate the multimedia device have software to generate the pop-out & sink-in 3D effects have a visual display capable of generating a pop-out & sink-in 3D effect, when viewed by the user of the 3D AR, VR, MR device.

have new virtual objects (2403) and ability to artificially insert new objects (2403) into the live image (2404) captured by the camera of the AR, VR, MR device where the new object (2403) and the live image (2404) are both displayed in pop-out & sink-in 3D where pop-out refers to the object seen as out of the screen and sink-in refers to as the object being below or behind the surface of the display screen.

have new virtual video to insert new video into the live image captured by the camera of the imaging device, where the new video and the live image are both displayed in pop-out & sink-in free space "pop-out" & "sink-in" hologram.

have the regular visual display screen converted to a pop-out & sink-in free space "pop-out" & "sink-in" hologram capable visual display by building or placing special optical device and component arrays on top of the visual display screen and thereby enabling glasses free viewing of free space "pop-out" & "sink-in" holograms.

have the regular visual display screen converted to a pop-out & sink-in free space "pop-out" & "sink-in" hologram capable visual display by building or placing a special optical screen on top of the regular visual display screen and thereby enabling glasses free viewing of free space "pop-out" & "sink-in" holograms.

have the visual display screen converted to a pop-out & sink-in free space "pop-out" & "sink-in" hologram capable visual display by building or placing a special optical filter on top of the regular visual display screen and thereby enabling glasses free hologram viewing.

have the regular display being converted to "pop-out" & "sink-in" display by means of using polarizing material on top of the regular visual display screen and using eye glasses to view the pop-out & sink-in free space "pop-out" & "sink-in" hologram images on the visual display screen.

have the images captured by the camera, converted to pop-out & sink-in free space "pop-out" & "sink-in" hologram images where when these images are displaced in a free space "pop-out" & "sink-in" hologram display, it can be viewed as pop-out & sink-in 3-Dimensional images just as humans see real world objects in 3 dimensional space. The images of objects superimposed onto the images captured by the camera are also converted to 3D friendly pop-out & sink-in "pop-out" & "sink-in" capable hologram images.

have the conversion of the normal image to "pop-out" & "sink-in" capable image is done by special software algorithms used with the "pop-out" & "sink-in" Augmented Reality device.

depending on the settings selected by the user, the depth where the object is placed can be adjusted so that the object can be either viewed as if it comes out or pops out from the visual display screen or sink into the screen.

have the capability by pointing the camera to a photo or an object, the AR, VR, MR device will start playing a pop-out or sink-in free space "pop-out" & "sink-in" hologram video on the Augmented reality (AR) device's screen as shown in FIGS. 21(*a*), 21(*b*).

have the capability by pointing the camera to a photo or an object, the AR or VR device will start playing a pop-out or sink-in free space "pop-out" & "sink-in" hologram video on the Virtual reality (VR) device's screen as shown in FIGS. 21(*a*), 21(*b*).

have the capability of free space "pop-out" & "sink-in" hologram device to function as a geographic Positioning system device known as GPS device, which can display maps in pop-out & sink-in free space "pop-out" & "sink-in" hologram (2502).

In one embodiment, the free space "pop-out" & "sink-in" hologram AR device (2501) is used for viewing street views (2502), maps, world maps, satellite imaging, birds' views, holographic perspectives.

Figure 27:
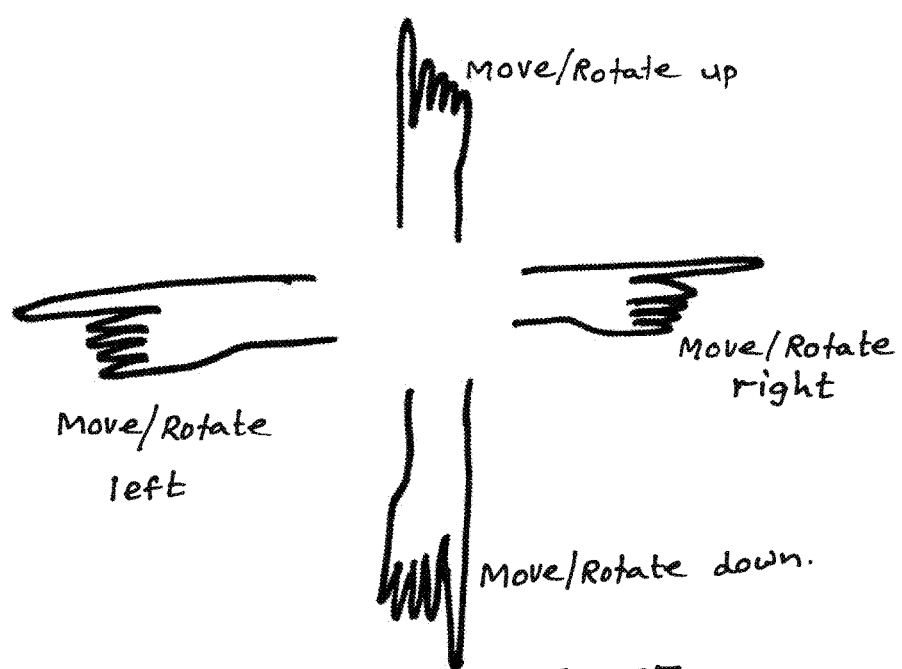
FIG. 27 illustrates gestures for gesture recognition.

In one embodiment, the free space "pop-out" & "sink-in" hologram (2601) device is used for simultaneous viewing of "pop out" or "sink in" 3D Augmented reality (AR) or Virtual reality (VR) or mixed (MR) reality (2602) by multiple people (2603), with a single device (2601). The free space "pop-out" & "sink-in" hologram (2602) is used with free space "pop-out" & "sink-in" hologram Augmented Reality (AR), free space "pop-out" & "sink-in" hologram Virtual Reality (VR) and free space "pop-out" & "sink-in" hologram mixed Reality (MR) functions, which is incorporated with gesture recognition as in FIG. 27, where the observer can make a certain gesture or for example, point his finger to a certain direction to rotate an object present in the AR, VR or MR device, to a certain direction. The gestures are not limited to pointing of a finger but can be used with a device which can be attached to the arm so that the arm movement can be detected and transmitted to the free space "pop-out" & "sink-in" hologram device which is used for free space "pop-out" & "sink-in" hologram manipulation, but not limited to these methods.

Figure 28:
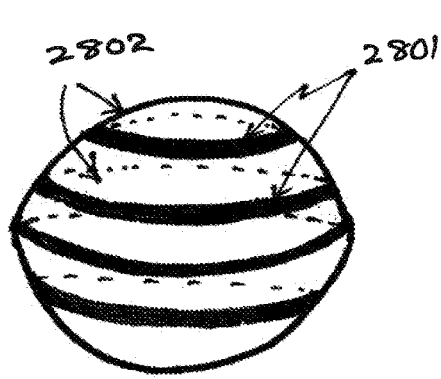
FIG. 28 illustrates juxtaposed rings of photochromic or thermochromic or magnetochromic or electrochromic material are painted or fabricated on a lens.
Figure 29A:
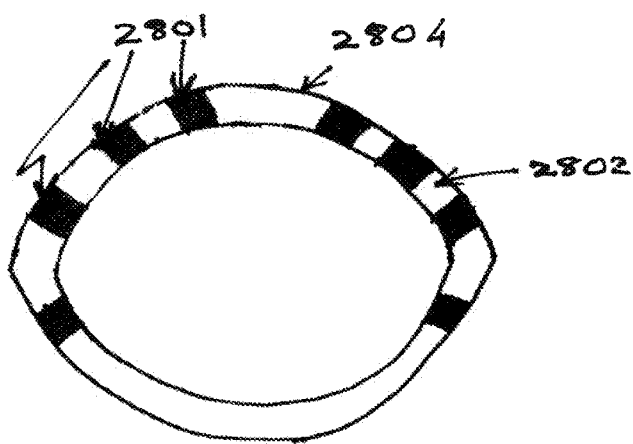
FIG. 29a illustrates the cross sectional view of the juxtaposed rings of photochromic or thermochromic or magnetochromic or electrochromic material which are painted or fabricated on a converging lens.
Figure 28A:
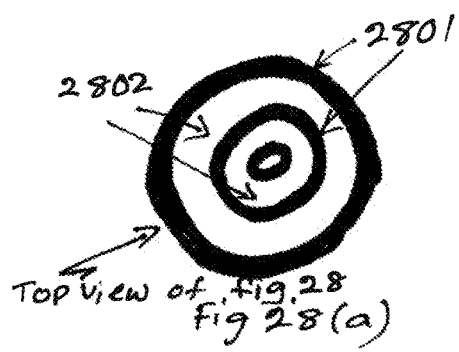
FIG. 28a illustrates the top view of the juxtaposed rings of photochromic or thermochromic or magnetochromic or electrochromic material are painted or fabricated on a lens.
Figure 29B:
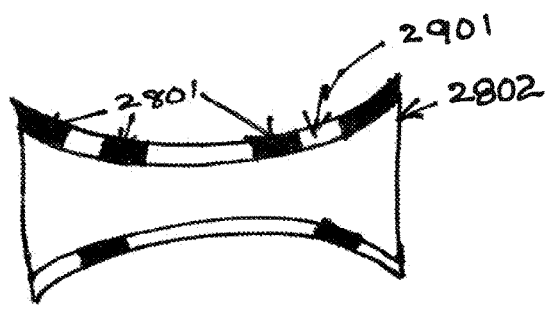
FIG. 29b illustrates the cross sectional view of the juxtaposed rings of photochromic or thermochromic or magnetochromic or electrochromic material which are painted or fabricated on a diverging lens.
Figure 30:
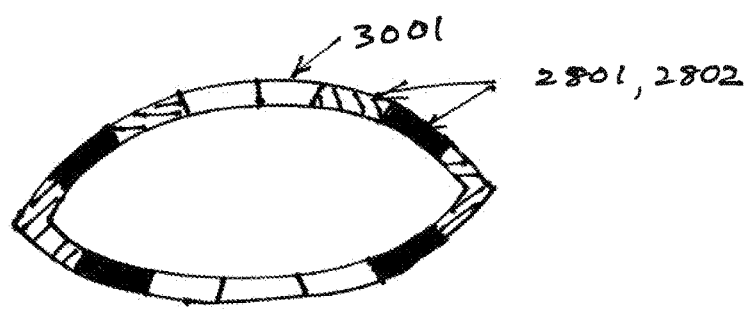
FIG. 30 illustrates juxtaposed rings of photochromic material painted or fabricated on the lens which are selectively turned to be opaque in such a manner that the rings towards the outer edge first become opaque and extends towards the rings which are more towards the middle of the lens, when the light intensity gradually increase thereby making the aperture smaller gradually, mimicking the pupil of the human eye.

In one embodiment, Juxtaposed rings (2801) & (2802) of photochromic or thermochromic or magnetochromic or electrochromic material are painted or fabricated on the lens (2802) as shown in FIG. 28. Cross sectional view of a converging lens of FIG. 28 as an example is shown in FIG. 29(*a*), FIG. 29(*b*) but not limited to these types of lenses and the top view of the lens is as FIG. 30, but not limited to this pattern or design. Photochromic material changes it's opacity with the change of light intensity and thermochromic material changes it's opacity with the change of temperature and magnetochromic material changes it's opacity with the change of magnetic field and electrochromic material changes it's opacity with the change of electric field. When photochromic material is used for the rings and when the light intensity is lower than a pre-determined value, all the rings are transparent and the aperture (3001) of the lens is at it's maximum. When the light intensity increases the painted photochromatic rings (2801) (2802) become opaque. The rings can be selectively turned to be opaque in such a manner that the rings towards the outer edge first become opaque and extends towards the rings which are more towards the middle of the lens, when the light intensity gradually increase thereby making the aperture smaller gradually as in FIG. 30, mimicking the pupil of the human eye. Similarly as described above, depending on the material used for the rings, the thermochromic rings, magnetochromic rings or electrochromic rings can be made opaque selectively, by applying heat, a magnetic field, an electric field respectively. The photochromic rings can be made to be opaque by the light coming from the field of view and it's surroundings and which is incident on the rings, thereby forming a self sufficient smart aperture (3001). For the thermochromic or magnetochromic or electrochromic based aperture rings will have to be controlled by using external or internal stimulants such as heat, magnetic field, electric field respectively, with the utilization of feedback techniques to determine the quantity of the stimulant to be applied. By using combinations of these variable aperture/variable focus lenses, very high quality camera is made which can capture images with very high image quality and image details which can easily capture 3D hologram capable images and videos, where all objects in it's field of view are in focus. In order to activate the thermochromic or magnetochromic or electrochromic based aperture rings, it may require providing electricity to the activator of the rings (2801), (2802), as an example for thermochromic rings will need a electric heater element to activate the rings. In order to provide electricity on the surface of the lens, optically transparent electrodes such as Indium Tin Oxide is used, but not limited to Indium Tin Oxide. FIG. 28, FIG. 29 (*a*), FIG. 29 (*b*), FIG. 30 shows the Juxtaposed aperture rings on the surface of the converging lens, cross section of the converging lens and cross section of the diverging lens respectively. Top view of the lens shown in FIG. 28 is as FIG. 28 (*a*). Some zone ring designs are as in FIG. 30.

Figure 30A:
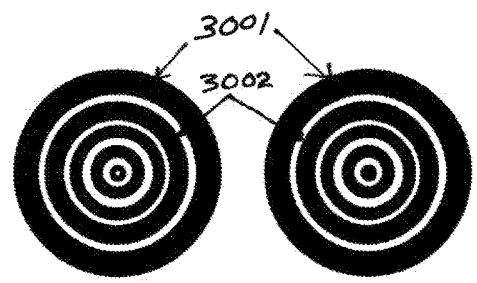
FIG. 30a illustrates a binary zone plate.
Figure 30B:
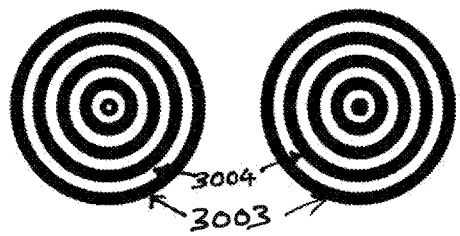
FIG. 30b illustrates a sinusoidal zone plate
Figure 31:
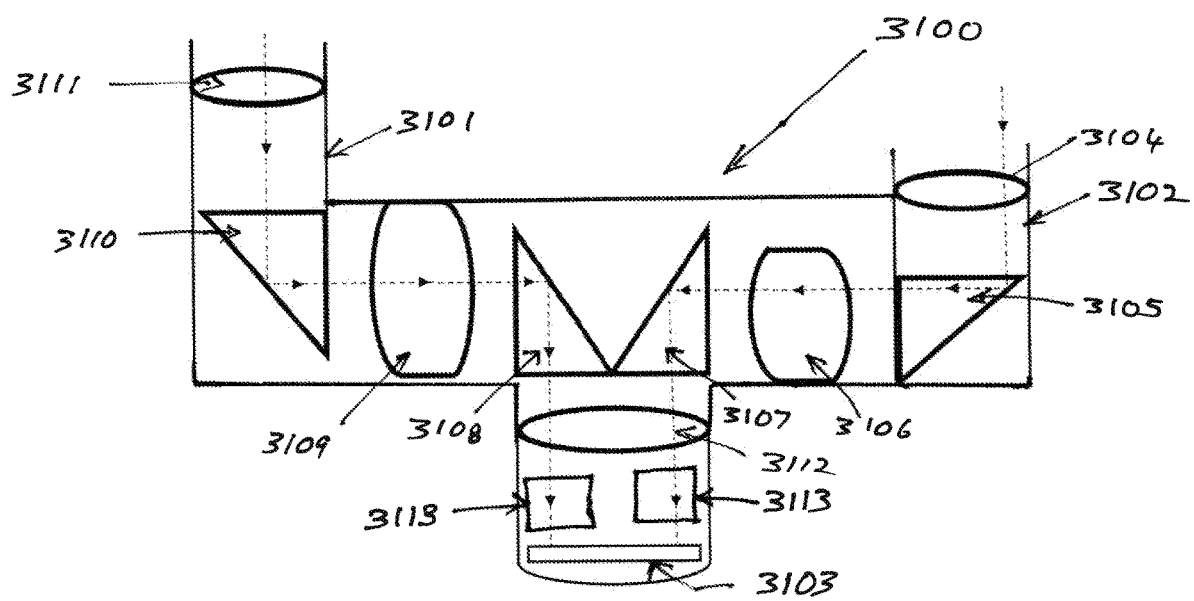
FIG. 31 illustrates the schematic diagram of the camera which can capture "pop-out" & "sink-in" hologram capable images and videos.

In one embodiment, The above described photochromic or thermochromic or magnetochromic or electrochromic juxtaposed rings are used as a variable focus zone plate lens or a variable focus Fresnel zone lens for focusing of images in a photographic camera, by making alternate rings opaque and transparent by means of the appropriate stimulant such as light, heat, magnetic field or electric field. These rings can either be concentric or acentric rings. These rings can also be operated in such a way that a few of adjacent rings can be made to be transparent while the next few rings can be made to be opaque in a repetitive manner as in FIG. 30*a* & FIG. 30*b*, by applying the appropriate stimulant to the rings selectively, depending on the material used for the rings, in order to make it operate as a compound lens with the lens on which the rings are painted, printed or fabricated. These rings in FIG. 30*a* & FIG. 30*b* which can be selectively made transparent or opaque by means of applying a stimulant is used to make Binary zone plate where the surface areas (3001) (3002) are equal for each and every transparent and opaque ring where these rings alternate between opaque and transparent. Similarly, a Sinusoidal zone plate is made by making the width of each opaque and transparent ring (3003) (3004) equal. A series of lenses or a lens system formed by a collection of above mentioned compound lenses is used to form zoom lens or a stack of suitably spaced above described zone plates or the stack of suitably spaced above described zone plates combined with regular lenses are used to form focus & zoom lenses. By using combinations of these smart variable apertures/variable focus/variable zoom lenses described above, very high quality camera (3100) is made which can capture images with very high image quality and image details which can easily capture 3D hologram capable images and videos, where all objects in it's field of view are in focus, where these cameras can be used on mobile devices, clinical diagnostic equipment, engineering applications, space applications such as in satellites & space vehicles, web cams, surveillance & security cameras, body cameras, wearable cameras, car cameras, car dash cameras, endoscopes and endoscopic capsule camera and device or application which requires a camera or the acquisition of images or videos.

In one embodiment, the above optical lenses in conjunction with other optical lenses are used to make a free space "pop-out" & "sink-in" hologram camera (3100) with hologram zoom, which has multiple arms (3101) (3102) attached onto the camera (3100), Using only one image sensor (3103), multiple combined optical modules (3104) (3105) (3106) (3107) (3108) (3109) (3110) (3111) (3112) (3113), multiple images from multiple viewpoints are captured simultaneously by using an optical system where it uses multiple prisms (3105) (3110) or mirrors (3105) (3110) to get total internal reflection of light or reflection of light respectively, in order to turn, guide and transmit the light from multiple directions on to a single image sensor (3103), through a combination of lenses, apertures and zone plates. Using only one image sensor provides the following added benefits to the camera to overcome issues of image sensor synchronization & timing, colour balancing & matching, frame synchronization, exposure correction to list a few but not limited to these. Side-by-Side or Up-Down or Side-by-Side-Up-Down images or videos can be recorded by this camera.

In one embodiment, the free space "pop-out" & "sink-in" hologram device consists of video and still image processing technologies and algorithms which incorporates image and video processing using one or more of the methods and processes such as translation, transforms, transformations, sine transformation, cosine transformation, tan transformation, inverse sin cos tan transformations, rotary transformations, fourier transform, double split transforms, but not limited to these.

Figure 32A:
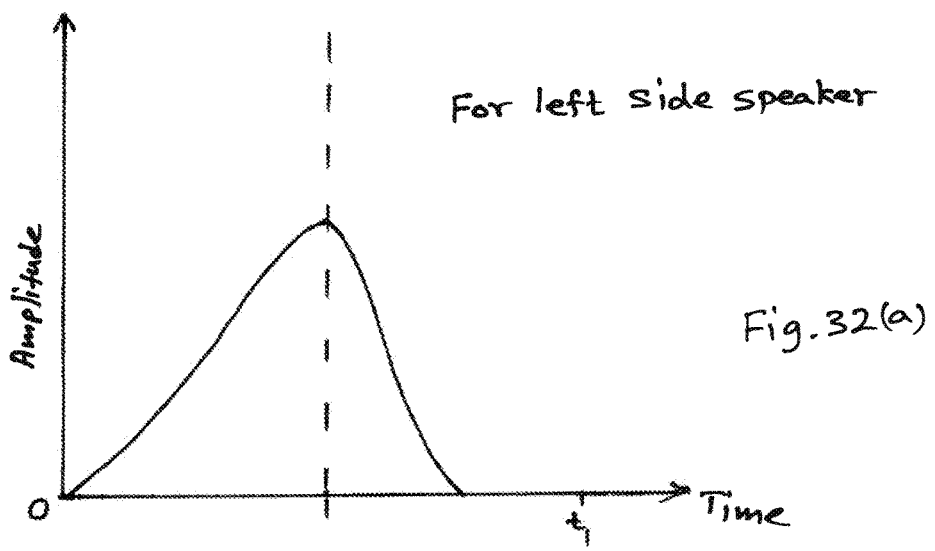
FIG. 32 illustrates the amplitude and frequency measurements to generate spatial audio effects.
Figure 32B:
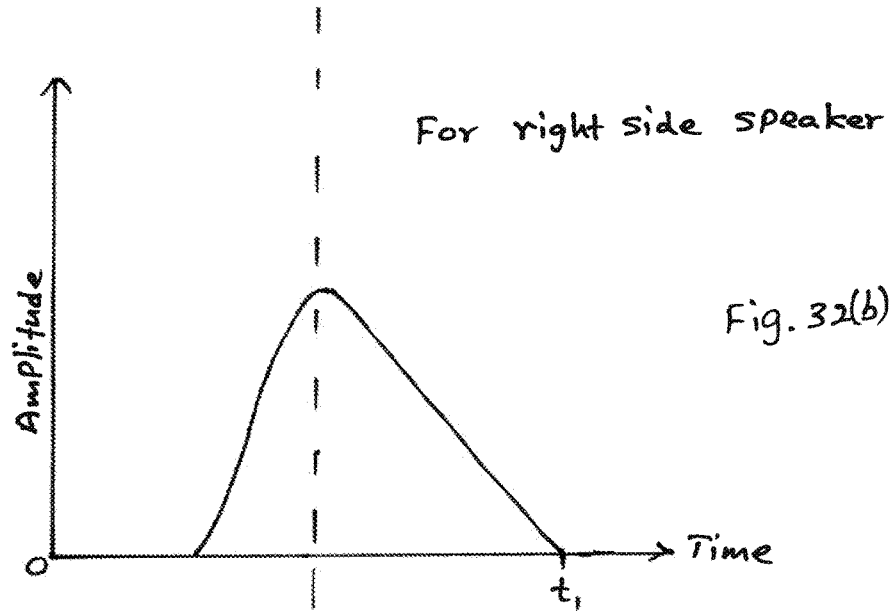
Figure 32C:
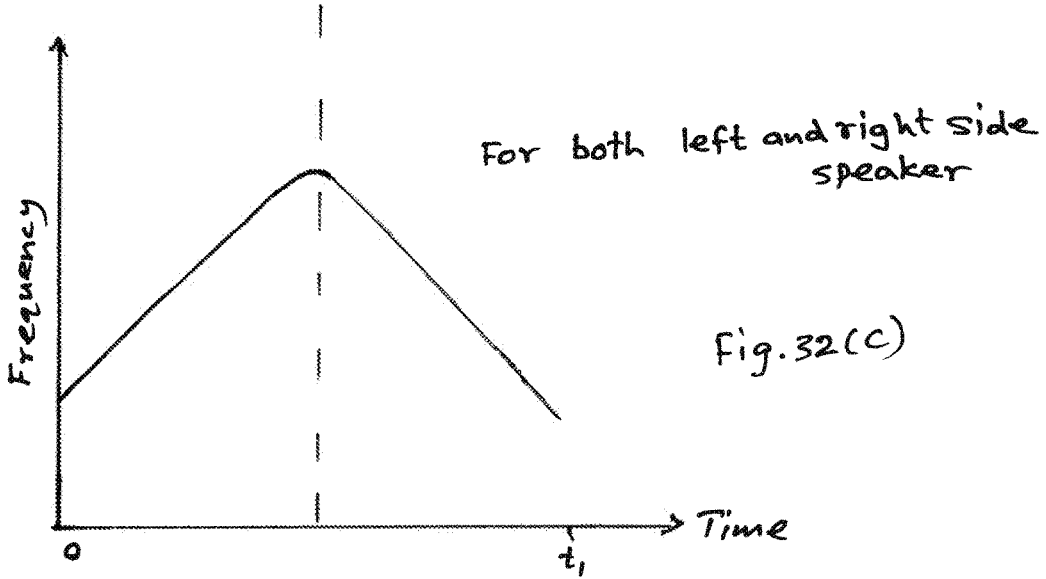
Figure 33:
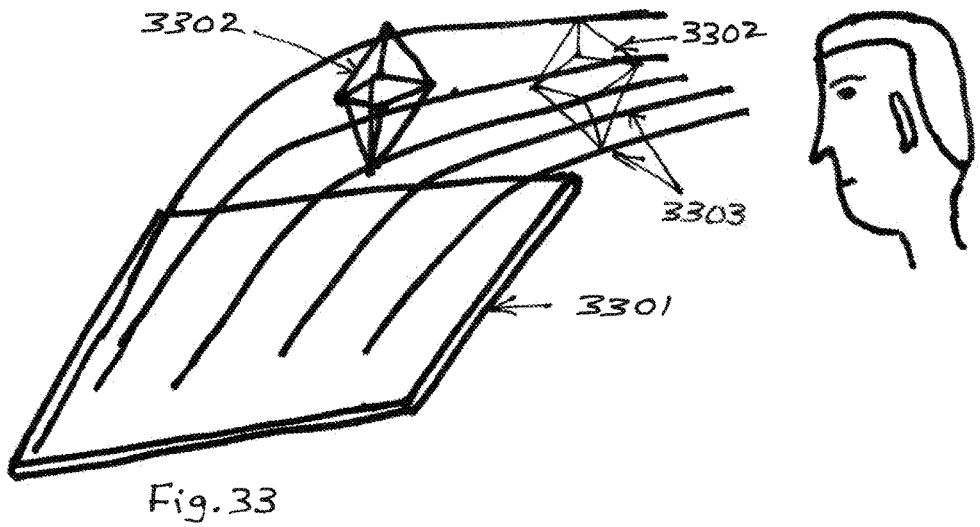
FIG. 33 illustrates the bending of light to generate the free space hologram.
Figure 33A:
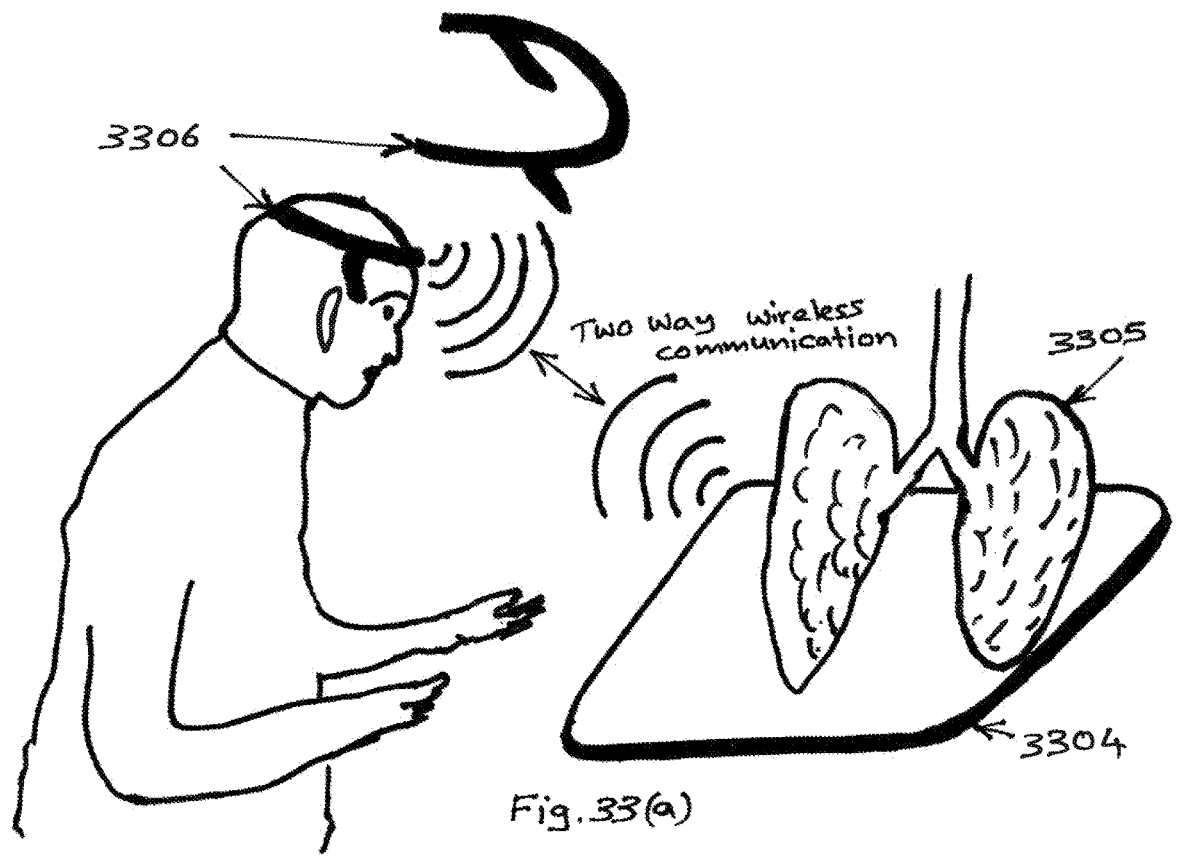
FIG. 33a illustrates the free space "pop-out" & "sink-in" hologram device being manipulated by means of using and incorporating brain wave detection and command technology or electroencephalography.
Figure 34:
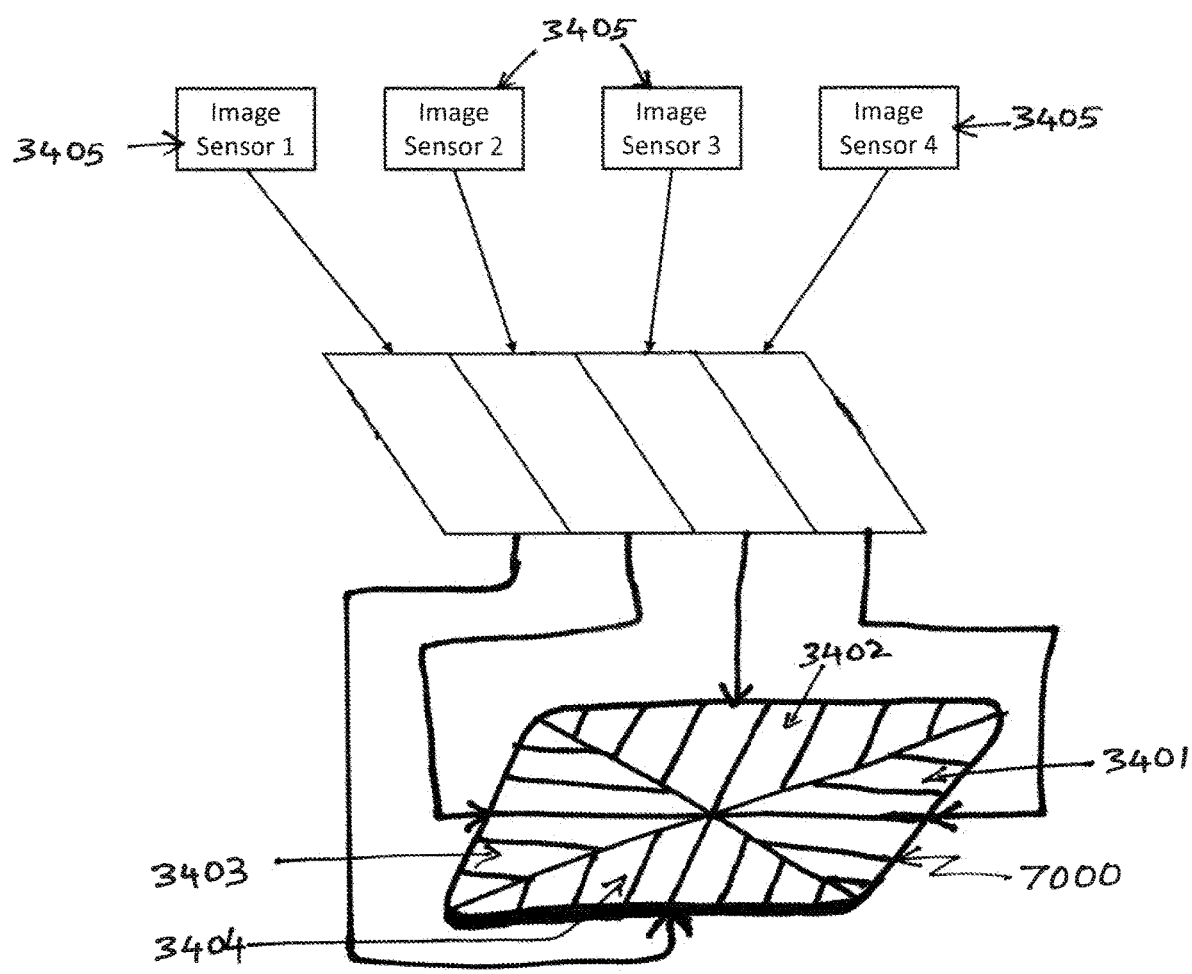
FIG. 34 illustrates multiple cameras or multiple image sensors being used to create multiple side-by-side (SBS) multi view free space "pop-out" & "sink-in" holograms is used for capturing the front view, back view, side views, top view and bottom view and these views which are fed into the free space "pop-out" & "sink-in" hologram to generate the 360 degree free space "pop-out" & "sink-in" hologram.

In one embodiment, the spatial audio, which can enhance the free space "pop-out" & "sink-in" hologram experience simulate real life auditory effects is incorporated into the free space "pop-out" & "sink-in" hologram. This audio provides multi-dimensional multi-directional audio effects. The effect is obtained by controlling the audio parameters such as but not limited to amplitude, frequency, treble, etc. Here, for example, to simulate a vehicle moving from left side to the right side by means of spatial audio, the amplitude of the sound of the vehicle is gradually increased on the left side headphone or speaker while for right side headphone or speaker the amplitude of the sound increased at a much lower amount or rate, until both amplitudes become equal when the vehicle is at the front of the observer or the middle of the display screen as seen in FIG. 32 (a), but not limited to this. Subsequently, when the vehicle continue to travel to the right side of the screen or passing the observer, the amplitude at the left side speaker or headphone is gradually decreased while the amplitude of the right side speaker or headphone is gradually reduced to zero as seen in FIG. 32 (b), but not limited to this. Similarly, frequency is adjusted to incorporate the well known Doppler effect which enhances the natural feeling of the audio regeneration. The frequency is gradually increased when the vehicle is moving towards the observer or the centre of the screen, until the vehicle comes to the front or middle of the screen and gradually decreased when the vehicle is moving away from the observer or the centre of the screen as seen in FIG. 32 (c), but not limited to this.

In one embodiment, light is bent selectively by means of magnetic fields created by an array of magnetic field generators placed on the surrounding area or under or on the surface or above the free space hologram display (3301). The magnetic field generators are not limited to electromagnetic field generators. The bending of the light beams' path (3303) in free space enabled the creation of the free space "pop-out" & "sink-in" hologram (3302).

In one embodiment, the free space "pop-out" & "sink-in" hologram device (3304) is manipulated by means of using and incorporating brain wave detection and command technology or electroencephalography and audio recognition. The brain waves which relate to the particular manipulation of the free space "pop-out" & "sink-in" hologram is detected using electrodes or a headset (3306) attached to the head or other relevant body part of the living person/animal and then the detected brain wave is analysed and is transformed and a relevant command is transmitted to the free space "pop-out" & "sink-in" hologram device via a wireless transmission method and then, upon receiving of the command by the free space "pop-out" & "sink-in" hologram device, the relevant intended change in the hologram (3305) is done. Brain wave detection and command technology is useful for this device since for example, during a surgery the surgeons will be able to operate/manipulate/turn/rotate the X-rays, CAT scans or MRI scans (3305) or access any other information on the free space "pop-out" & "sink-in" hologram device (3304), by using surgeon's brain wave detection, without requiring them to use hands or voice. Furthermore, the free space "pop-out" & "sink-in" hologram device can send information to the surgeon via the brain wave detection and command technology, through the electrodes attached to the head of the person with the aid of the headset (3306). Similarly, signals from different body parts can be used to manipulate the "pop-out" & "sink-in" hologram device, but not limited to these signals. Similarly, the "pop-out" & "sink-in" hologram device can send signals directly to the users brain via the wireless enabled brain wave headset, to stimulate and communicate with the brain.

In one embodiment, multiple cameras or multiple image sensors (3405) are used to create multiple side-by-side (SBS) multi view free space "pop-out" & "sink-in" holograms is used for capturing the front view, back view, side views, top view and bottom view and these views are fed into for example but not limited to, the display panel's pre-determined multiple specific areas (3401) (3402) (3403) (3404) to generate the 360 degree free space "pop-out" & "sink-in" hologram.

In one embodiment, the free space "pop-out" & "sink-in" hologram display device is used to project two or more different movies or pictures in free space "pop-out" & "sink-in" hologram simultaneously, which can be watched by two or more viewers, where each viewer can watch one movie at a given time, without having any interference from the other free space "pop-out" & "sink-in" hologram movie or photo.

What is claimed is:

1. A hologram device comprising a hologram display panel which generates, creates and displays a free space pop-out and sink-in hologram on a surface of, or on top of, or inside of, or partially on top of and partially inside of, the hologram display panel, wherein the hologram display panel comprises one or more layers containing special materials having different optical properties and features, the one or more layers being attached to the hologram display panel, wherein the one or more layered structure attached to the hologram display panel generates, creates, and displays the hologram in free space;

wherein the hologram display panel comprises a Liquid Crystal Display (LCD) based, Light Emitting Diode (LED) based, electronic paper based, digital paper based, light based, Cathode Ray Tube (CRT) based, pixelated based, or an illuminated based, display; and wherein the one or more layers comprise one or more of the following: optical focusing layer & structure, optical lens array, optical refractive layer and structure, optical diffraction layer, optical guide layer and structure, optical total internal reflection structure layer, optical total internal reflection layer, optical spacer layer, diverging optics layer, converging optics layer, lenticular optics layer, array of optical total internal reflective structures, adhesive layer, optical coupling layers, optical adhesive coupling layer, electromagnetic or electro static actuators for fine tuning of hologram, hydraulic or pneumatic actuator for fine tuning of hologram, mobile phone communication hardware, antenna for wireless communication, batteries, cellular network hardware and software, magnetic field inducer array, single or multiple cameras for eye tracking, display with an array of pixels, backlight for display illumination, backlight illumination with quantum dots, color filter and filter array, camera capable of capturing 3-dimensional hologram quality fully focused images and videos, and spatial audio.

2. The hologram device of claim 1, wherein the hologram display panel is capable of displaying a free space pop-out and sink-in hologram in at least one of: 3-dimensional augmented reality (AR), virtual reality (VR), and mixed reality (MR).

3. A multimedia device comprising the hologram device of claim 2, and further comprising:
(a) a camera having a camera lens for capturing a 3-dimensional hologram capable image, where the camera lens mimics a human eye by changing its lens aperture according to the light intensity, camera lens focuses, and the camera captures a 3-dimensional image suitable for generating, creating, and displaying, a free space pop-out and sink-in hologram;
(b) software to operate the multimedia device;
(c) software to generate the pop-out and sink-in 3-dimensional effects; and
(d) a visual display capable of displaying a pop-out and sink-in 3-dimensional effect, when viewed by a user of the multimedia device.

4. The hologram device of claim 1, wherein the one or more layers further comprise one or more of the following: combined array of lenses and mirrors, array of prisms, array of lenses, array of mirrors, array of lenticules, array of lenticular lenses, array of convex lenses, array of concave lenses, array of diverging lenses, array of converging lenses, array of multi faced structures, array of multi faced lenses, array of multi faced mirrors, array of actuators, array of electromagnetic filters, array of color filters, array of polarizers, optical spacer arrays or layers, array of optical filters, array of optical total internal reflecting structures, array of hydrophilic areas, array of hydrophobic areas, array of both a combination of hydrophilic and hydrophobic areas, array of liquid lenses of various shapes and kinds, array of diverging optics, array of converging optics, array of lenticular optics, array of electromagnetic inductors, and magnetic field inducer array.

5. The hologram device of claim 4, wherein the one or more layers further comprise one or more of the following: array of lenticules, array of lenticular lenses, array of hydrophilic areas, array of hydrophobic areas, array of a combination of hydrophilic and hydrophobic areas, and array of liquid lenses of various shapes and kinds.

6. The hologram device of claim 1, wherein the hologram display panel further comprises liquid lenses or liquid lens arrays on the surface of the display screen in order to create the free space hologram, wherein the liquid lenses are created by patterning hydrophilic and hydrophobic areas on the surface of the display and applying the liquid onto this patterned surface, thereby creating lenses on the hydrophilic areas by self-formation of liquid lenses on the hydrophilic areas.

7. The hologram device of claim 1, wherein the hologram display panel comprises different optical patterns or material or structures on top of the display screen in multiple directional patterns in order to make a full around free space pop-out and sink-in hologram where an observer can view the front, back, and two side views of the hologram.

8. The hologram device of claim 1, wherein the hologram display panel is a foldable hologram display panel where when the display panel is folded it appears as a closed device and the hologram is not displayed, and when it is open the hologram is displayed.

9. The hologram device of claim 8, wherein the foldable hologram display panel is a hologram book, a foldable tablet, a foldable monitor, a foldable television, or a foldable phone.

10. The hologram device of claim 8, wherein the foldable hologram display panel comprises two or more hologram display screens joined together with hinges to create the foldable hologram display.

11. The hologram device of claim 1, wherein the hologram device is connected to a device or component where specially processed video signals or still images are generated and delivered to an input of the hologram display panel.

12. The hologram device of claim 11, wherein the device or component's connection is through wi-fi, bluetooth, 2G, 3G, 4G, or 5G.

13. The hologram device of claim 1, wherein the hologram device is embodied as a smart wristwatch having phone and wireless broad band functions.

14. The hologram device of claim 1, wherein the hologram display panel can be turned ON or turned OFF by using a hardware 4-way switch or a 4-way soft switch, whereby the hologram display may be toggled between 2-dimensional mode, 3-dimensional sink-in mode, 3-dimensional pop-out mode, and free space pop-out and sink-in mode.

15. The hologram device of claim 1, wherein the one or more layers comprise spatial audio which simulates real life auditory effects.

16. The hologram device of claim 1, further comprising video and still image processing technologies and algorithms which include one or more video and image processing methods selected from translation, transforms, transformations, sine transformation, cosine transformation, tangent transformation, inverse sin cosine tangent transformations, rotary transformations, Fourier transform, and double split transforms.

17. The hologram device of claim 1, wherein the one or more layers comprise one or more of the following: optical lens array, optical spacer layer, lenticular optics layer, electromagnetic or electrostatic actuators for fine tuning of hologram, hydraulic or pneumatic actuator for fine tuning of hologram, single or multiple cameras for eye tracking, and camera capable of capturing 3-dimensional hologram quality fully focused images and videos.

18. The hologram device of claim 17, wherein the one or more layers comprise one or more of the following: optical spacer layer, and lenticular optics layer.

19. A multimedia device comprising an Augmented Reality (AR) device or a Virtual Reality (VR) device or a Mixed Reality (MR) device, and a hologram device, wherein the hologram device comprises a hologram display panel which generates, creates and displays a free space pop-out and sink-in hologram on a surface of, or on top of, or inside of, or partially on top of and partially inside of, the hologram display panel:
  wherein the hologram display panel comprises one or more layers containing special materials having different optical properties and features, the one or more layers being attached to the hologram display panel, wherein the one or more layered structure attached to the hologram display panel generates, creates, and displays the hologram in free space;
  wherein the one or more layers comprise one or more of the following: optical focusing layer & structure, optical lens array, optical refractive layer and structure, optical diffraction layer, optical guide layer and structure, optical total internal reflection structure layer, optical total internal reflection layer, optical spacer layer, diverging optics layer, converging optics layer, lenticular optics layer, array of optical total internal reflective structures, adhesive layer, optical coupling layers, optical adhesive coupling layer, electromagnetic or electro static actuators for fine tuning of hologram, hydraulic or pneumatic actuator for fine tuning of hologram, mobile phone communication hardware, antenna for wireless communication, batteries, cellular network hardware and software, magnetic field inducer array, single or multiple cameras for eye tracking, display with an array of pixels, backlight for display illumination, backlight illumination with quantum dots, color filter and filter array, camera capable of capturing 3-dimensional hologram quality fully focused images and videos, and spatial audio; and
  wherein the hologram display panel is attached to the AR, VR, or MR device's regular display screen.

20. The multimedia device of claim 19, wherein the one or more layers comprise one or more of the following: optical lens array, optical spacer layer, lenticular optics layer, electromagnetic or electrostatic actuators for fine tuning of hologram, hydraulic or pneumatic actuator for fine tuning of hologram, single or multiple cameras for eye tracking, and camera capable of capturing 3-dimensional hologram quality fully focused images and videos.

* * * * *